United States Patent [19]

von Behrens et al.

[11] Patent Number: 5,378,633

[45] Date of Patent: Jan. 3, 1995

[54] METHOD FOR ACCURATELY ENUMERATING AND SENSITIVELY QUALIFYING HETEROGENOUS CELL POPULATIONS IN CYTOLYTIC PROCESSING CONDITIONS

[75] Inventors: Wieland E. von Behrens, Hillsborough; Sherry Haiflich, San Carlos, both of Calif.; John Glazier, Penbroke Pines, Fla.; John M. Roche, Morgan Hill; Bruce A. Director, Santa Clara, both of Calif.

[73] Assignee: Sequoia-Turner Corporation, A Corp. of CA, Mountain View, Calif.

[21] Appl. No.: 197,575

[22] Filed: Feb. 16, 1994

Related U.S. Application Data

[63] Continuation of Ser. No. 832,471, Feb. 7, 1992, abandoned.

[51] Int. Cl.⁶ ............................................. G01N 33/48
[52] U.S. Cl. ........................................ 436/63; 436/17; 436/34; 436/164; 356/39
[58] Field of Search ................. 436/10, 17, 18, 34, 436/150, 164, 63; 435/7.21, 7.24, 7.25, 2; 356/39

[56] References Cited

U.S. PATENT DOCUMENTS

| | | | |
|---|---|---|---|
| 3,606,539 | 9/1971 | Polanyi et al. | 356/39 |
| 3,871,770 | 3/1975 | von Behrens et al. | 356/103 |
| 4,040,742 | 8/1977 | Ito et al. | 356/39 |
| 4,425,427 | 6/1984 | Luderer et al. | 435/10 |
| 4,448,771 | 5/1984 | Cattani et al. | 424/180 |
| 4,506,018 | 3/1985 | North, Jr. | 436/10 |
| 4,521,518 | 6/1985 | Carter et al. | 436/10 |
| 4,637,986 | 1/1987 | Brown et al. | 436/10 |
| 4,710,021 | 12/1987 | von Behrens | 356/72 |
| 4,745,071 | 5/1988 | Lapicola et al. | 436/63 |
| 4,751,179 | 6/1988 | Ledis et al. | 435/34 |
| 4,882,284 | 11/1989 | Kirchanski et al. | 436/63 |
| 4,902,613 | 2/1990 | Chang et al. | 435/2 |
| 4,933,293 | 6/1990 | Kuroda et al. | 436/63 |
| 4,962,038 | 10/1990 | Carter et al. | 436/10 |
| 4,978,624 | 12/1990 | Cremins et al. | 436/17 |
| 5,017,497 | 5/1991 | Gerard de Grooth et al. | 436/63 |
| 5,039,613 | 8/1991 | Matsuda et al. | 436/17 |
| 5,045,474 | 9/1991 | Becker et al. | 346/63 |

FOREIGN PATENT DOCUMENTS

| | | |
|---|---|---|
| 0115077 | 8/1984 | European Pat. Off. |
| 0259833 | 3/1988 | European Pat. Off. |
| 0444241A1 | 3/1990 | European Pat. Off. |

OTHER PUBLICATIONS

W. E. von Behrens, "Mediterranean Macrothrombocytopenia," Blood 45:199 (1975).

(List continued on next page.)

*Primary Examiner*—James C. Housel
*Assistant Examiner*—Maureen M. Wallenhorst
*Attorney, Agent, or Firm*—Richard D. Schmidt

[57] ABSTRACT

A method for identifying, characterizing, categorizing and enumerating cells within a cell population. The survivorship characteristics of the different cell populations is used to obtain quantitative and qualitative information about the cell populations initially present in the sample solution before conditions were imposed on the sample solution to elicit a response. The monitored cell survivorship response may be either direct disappearance of intact cells or the appearance of cell structures, carcasses, ghosts or residuum. In a preferred embodiment, a leukocyte cell decay rate in the presence of an erythrolytic agent is determined by monitoring leukocyte counts at several time intervals after the addition of the erythrolytic agent to the sample solution. The leukocyte decay rate is then used to indicate the presence of a fragile leukocyte population, and to accurately estimate the number of leukocytes initially present in the whole blood sample. The use of stronger erythrolytic agents in samples with lyse-resistant erythrocytes while preserving the accuracy of leukocyte counts is allowed. The present method permits calculation of a leukocyte decay rate which can be back extrapolated to time zero to provide an accurate estimate of the leukocyte count initially present in the whole blood sample.

79 Claims, 12 Drawing Sheets

OTHER PUBLICATIONS

W. E. von Behrens, "Homogeneous Heterogeneity of Platelet Populations," Proc. Aust. Soc. Med. Res. 2:339, 1970.

W. E. von Behrens and Edmondson, "Comparison of Techniques Improving the Resolution of Standard Coulter Cell Sizing Systems," J. Histochem. & Cytochem. 24:247–256 (1976).

H. Begemann, J. Rastetter, "Atlas of Clinical Hematoology," p. 227 4th Ed. (1989) (Springer-Verlag).

J. Cross, C. A. Strange, "Erroneous Ortho ELT 800/WS WBC in chronic lymphatic leukaemia," Clin. Lab. Hematol. 9:371–375 (1987).

Approved Standard,; "Reference Leukocyte Differential Count (Proportional) and Evaluation of Instrumental Methods", NCCLS Document H20-A (1991) (Villanova, Pa.).

Lewis, S. M., "Automated Differential Leukocyte Counting: Present Status and future Trends," Blut 43:1–6 (1981).

Kupach H. R., Mieth K.; "Comparison of Methods of Counting Leukocytes and Lymphocytes and their Suitability for the Diagnosis of Bovine Leukosis part 1," Arch. Exp. Veterinaermed 24(6):1277–1282 (1970).

C. M. Densmore, "Eliminating Disintegrated Cells on Hematologic Smears," Lab. Med. 12:640–41 (1981).

J. B. Dixon et al., "Electronic Counting of Dog Leukocytes. Discrepancies Arising From Calibration With Coulter Standard 4C and With the Hemocytometer," Res. Vet. Sci. 31(2):249–252 (1981).

J. M. England, et al., "An assessment of the Ortho ELT-8," Clin. Lab. Hematol., 4:187–199 (1982).

A. Bremmelgaard, J. Nygard, "Interfernece by Cryoglobulin with White Blood Cell Measurements on Coulter Counter," Scand. J. Clin. Lab. Invest. 51(5):489–492 (1991).

W. E. von Behrens and Lander, Proc. Australian Soc. Med. Research, 2:380 (1970).

Dzik W. H., Ragosta A., "Flow–cytometric Method for Counting Very Low Numbers of Leukocytes in Platelet Products," Vox Sang 59(3):153–159 (1990).

Scott, Mark D., Kuypers, Fran A., "Effect of osmotic lysis and resealing on red cell structure and function," J. Lab. Chem. vol. 115(4):470–480 (1990).

von Behrens, W. E., "Additional Morphologic Parameters for the Routine Complete Blood Picture"; Clinical Research 22:123A (1974).

Carter, P. H., "Flow Cytometric analysis of Whole Blood Lysis, Three Anticoagulants, and Five Cell Preparations," Cytometry 13:68–74 (1992).

FIG. 2

SALTATORY          JUMP

DRIFT

METHOD FOR ACCURATELY ENUMERATING AND SENSITIVELY QUALIFYING HETEROGENOUS CELL POPULATIONS IN CYTOLYTIC PROCESSING CONDITIONS

This is a continuation of U.S. application Ser. No. 07/832,471, filed on Feb. 7, 1992, now abandoned.

TECHNICAL FIELD

The present invention relates generally to cytology and to the use of automated instruments to enable accurate categorization and enumeration of specific cell types present in cell suspensions. The invention also enables the refined functional identification and characterization of cell types present in cell suspensions. More specifically, this invention relates to methods which enable the accurate categorization, characterization, identification and enumeration of cell populations which may be unstable in a saltatory manner under otherwise desirable sample processing conditions. Such cell populations include fragile and lyse-sensitive blood cells which undergo sudden large changes as a result of an abnormal cell condition or as a result of the use of strongly cytolytic processing agents and conditions (or through interaction of such factors).

BACKGROUND OF THE INVENTION

Prior investigators recognized that mixed cell suspensions can be analyzed for the presence or absence of cell populations and for quantitative information concerning the number of specific types of cells present in the sample. This information is useful in the diagnosis of disease and in the monitoring of the effectiveness of therapy for certain disease conditions. Prior investigators further recognized that detectable differences in cell population responses to conditions imposed upon the mixed cell suspension can be advantageously exploited to signal the presence or absence of specific cell populations. These detectable differential responses can also be used to generate signals which are unique to a single cell population, enabling enumeration of that cell population. The mixed cell systems in which differential response techniques have been studied include physiological fluids such as blood, blood plasma, bone marrow, semen and organ cell suspensions as well as cell culture media, including plant cell suspensions. Such response techniques range from differential cell staining in the presence of an added dye to failure of one or more cell populations to survive an imposed stress such as brief or prolonged exposure to an extreme in temperature, pH, tonicity or chemical microenvironment.

The selection of an imposed condition by which to generate a differential response from a mixed cell suspension is typically a compromise. The inherent similarities between cell populations present in the cell suspension inadvertently lead to some partial response from the untargeted cell population which adversely affects the quality of the information obtained in all such types of differential response techniques.

Mammalian blood is one of the more thoroughly studied mixed cell suspensions which is analyzed utilizing various differential response techniques-including a differential cell-population-survivorship response. The cell populations present in whole blood are the erythrocytes (E or red cells) whose concentration in mammals is in millions per microliter; the anucleate thrombocytes (T or platelets) whose concentrations in mammals is generally in tens to hundreds of thousands per microliter; and the nucleated leukocytes (or white cells) whose concentration in mammals generally ranges from hundreds per microliter to tens of thousands per microliter and sometimes beyond (for any sub-population of leukocytes). Leukocytes in peripheral blood of normal mammals are further classified into five major types or sub-populations: the smaller lymphocytes (L), and the larger neutrophils (Ne), eosinophils (Eo), basophils (Ba) and monocytes (Mo).

These blood cell populations are visible in FIG. 1 in which the neutrophils, eosinophils and basophils are collectively identified as granulocytes (G). All five major leukocyte subpopulations are shown in FIG. 6.

One of the major distinctions between erythrocytes and leukocytes is that, in health, it is relatively simple to identify erythrolytic agents which selectively destroy (or lyse away) the erythrocytes while leaving the typical leukocytes substantially intact. Enormous differences in cytoplasmic structure account for this differing survivorship response. When a leukocyte population in solution is presented with physico-chemical conditions which cause all the erythrocytes in the whole blood sample to exceed this critical hemolytic threshold, these erythrocytes in the whole blood sample will have been lysed away by a rapid cytolytic decay process which is mainly an interaction of osmotic, oncotic and surface membrane phenomena. It is predicted that, usually, all of the leukocyte subpopulations will also commence their own lytic decay processes. However, unlike mature erythrocytes, leukocytes (including thrombocytes) have a large amount of readily recruitable redundant internalized cell membrane. Under appropriate conditions, this membrane material can be externalized so that leukocytes share many of the characteristics of a soap bubble under inflation. Those soap bubbles which can still be inflated further still have readily recruitable, spare (non-surface) soap molecules in reserve. Erythrocytes which are more mature than reticulocytes no longer have any redundant surface material. As a result, by comparison with erythrocytes, the rate at which the members of the leukocyte populations reach their critical hemolytic threshold is generally so slow that, under many temporal conditions of analysis, leukocyte populations can be viewed as effectively lyse-resistant.

For over a century, this differing cell-survivorship response has been exploited haphazardly to permit categorization and enumeration of leukocytes present in a whole blood sample. It is evident from FIG. 1 that if the erythrocytes are simply lysed away, while the leukocytes and thrombocytes are preserved, then it is no longer necessary to process over ten thousand erythrocytes for every single member of the less numerous leukocyte subpopulations. This reduced processing burden greatly shortens the time (and cost) for analyzing a whole blood sample. However, exploitation of this differing cell-survivorship response to lytic agents in the century old techniques has very real limitations. A compromise must be struck between the use of strongly erythrolytic conditions which effect complete erythrolysis (at the cost of some leukocytes) and the use of less strongly erythrolytic conditions to leave the leukocytes unaffected (at the cost of impairing leukocyte counting because of the presence of unlysed interfering erythrocytes). Over the last one hundred fifty years, we have not found an optimum compromise condition which simultaneously addresses these conflicting responses in both health and disease.

Consequently, the cost-effective and rapid erythrolytic procedures advantageous for automation in human and veterinary clinical use are also intrinsically leukolytic (white cell and platelet lysing). The accurate categorization and enumeration of leukocyte subpopulations can thereby be compromised. The leukolytic activity accompanying erythrolysis degrades the clinical categorization and enumeration of the leukocyte subpopulations since the accuracy of the count is greatly reduced. Therefore, it is one object of the present invention to provide a method for categorizing and enumerating leukocyte subpopulations which method accounts for (and corrects the enumeration for) the inherent leukolytic activity of commonly used erythrolytic agents and conditions.

FRAGILE LYMPHOCYTES

The clinical value of any method for categorization and enumeration of leukocyte subpopulations is directly related to its utility in identifying and qualifying abnormal conditions existing in the erythrocyte and leukocyte populations which circulate in the blood in health and in disease. For example, in a few rare but very important clinical disorders, certain circulating leukocytic sub-populations may contain extremely lyse-sensitive members. "Fragile lymphocytes", as in certain cases of chronic lymphocytic leukemia and as in infectious mononucleosis, are a paradigm for this situation. In such clinical conditions, the morphologists of the last century identified "Gumprecht shadows" in the microscopic analysis of the blood film. See H. Begemann, J. Rastetter, *Atlas of Clinical Hematology*, 4th Edition 1989, p. 227 (Springer-Verlag). Today's technologists recognize "smear cells" (J. Cross, C. A. Strange, "Erroneous Ortho ELT 800/WS WBC in chronic lymphatic leukaemia," Clin. Lab. Hematol. 1987, 9, 371-375) or "smudge cells" (National Committee for Clinical Laboratory Standards. Reference Leukocyte Differential Count (Proportional) and Evaluation of Instrumental Method. Approved Standard, NCCLS Document H20-A 1992. (Villanova, Pa.) The affected leukocyte cell populations may contain cells which are so fragile that they cannot even be preserved in the blood film without the addition of a high concentration of a colloid (such as albumin) to the droplet of blood before the stress of the film-making process is imposed on the cells. NCCLS Document H20-A; Densmore, C. M. "Eliminating disintegrated cells on hematologic films" Lab. Med. 12:640-41, 1981. All the redundant internal membrane material of these cells is in such a highly dispersed state that it has an extremely significant oncotic activity and is not readily recruitable under hypotonically stressed conditions. These cells are analogous to the prolytic spheres of FIG. 2 (to be discussed later). The high oncotic pressure of the colloid in the diluent decreases the sphericity index of these prolytic lymphocytes. Hence they no longer pop under the shear press of the blood film smearing process.

Such very fragile leukocytic cells are also difficult to preserve when blood is greatly diluted and vigorously processed in the so-called flow-cytometric automated blood cell counters. This is true even when the diluent is an apparently balanced, (protein-free), physiologic salt solution that is intended to preserve rather than lyse the numerous interfering erythrocytes. Hence, when these fragile leukocytes are present in a sample, it is sometimes virtually impossible to know the correct circulating leukocyte concentration (or the total white cell count) and the correct numerical count for the leukocyte subpopulations. J. Cross, C. A. Strange, "Erroneous Ortho ELT 800/WS WBC in chronic lymphatic leukaemia," Clin. Lab. Hematol. 1987, 9, 371-76; J. B. Dixon et al., "Electronic Counting of Dog Leukocytes Discrepancies Arising From Calibration With Coulter Standard 4C and With the Hemocytometer," Res. Vet. Sci. 31 (2), 1981, 249-252; J. M. England, et al., "An assessment of the Ortho ELT-8," Clin. Lab. Hematol., 1982, 4, 187-99.

The present invention provides a method for identifying the presence of such fragile cells and for alerting a laboratory that leukocyte counts by other counting methods most likely underestimated the circulating count. It also provides a method for obtaining an accurate categorization and enumeration of leukocyte subpopulations and thereby of total leukocytes. These objectives are met by compensating sufficiently precisely for any leukocyte counting errors caused by inadvertent leukolysis during the data gathering phase of the analysis. The present method enables the use of quantitative data for qualitatively discriminating or classifying cell types.

LYSE-RESISTANT ERYTHROCYTES

Another important clinical dilemma which can be handled successfully by the methods of the present invention involves whole blood samples which contain so-called lyse-resistant erythrocytes. In one group of well known conditions which lead to lysis-surviving erythrocytes, the erythrocytes themselves appear difficult to lyse by the techniques applicable to typical human samples, e.g., sickle cell diseases, fetal and neonatal blood cells, and other atypical, aberrant physiologic mammalian erythrocyte populations. In another group of conditions or disorders, the presence of lysis-opposing interfering substances makes erythrocytes difficult to lyse under erythrolytic conditions which are effective for typical human samples. For example, an abnormally high concentration of blood proteins tends to neutralize some of the erythrolytic agents and to oncotically counteract some of the erythrolytic physical approaches. A. Bremmelgaard, J. Nygard, "Interference by Cryoglobulins with White Blood Cell Measurements on Coulter Counter," Scand J Clin. Lab. Invest. 51 5 1991, 489-492. Parenteral feeding solutions, certain blood lipid disorders and therapeutic drugs may also act to create erythroprotective conditions, either alone or in combination with other agents or with anomalous erythrocytes.

In the presence of failed or partial erythrolysis resulting from the problem of lyse-resistant erythrocytes, the entire leukocyte counting procedure may become invalid for affected samples. Lyse-surviving erythrocytes interfere with leukocyte visualization. If one percent of five million erythrocytes fails to lyse for every $\mu l$ of human blood, fifty thousand unlysed erythrocytes remain to obscure the five thousand nucleated leukocytes present in that representative $\mu l$ of human blood. Even though samples with as few as 0.1% residual erythrocytes can frequently be flagged by such instruments to distinguish them from normal blood samples, another method must be employed to count the leukocytes in these samples. Sometimes counts must be performed manually, but they are always performed at an increased cost in turnaround time, in equipment, in laboratory space, in direct labor, and above all, in laboratory expertise and in the complex protocols for these problem-sample procedures which must be developed, maintained and quality controlled. The dilemma is that use of a stronger erythrolytic agent or condition to achieve complete erythrolysis and to decrease the number of lyse-resistant erythrocytes results in an intolerable increase in leukolysis. Hence a hazardous compromise currently exists which achieves neither routine reliable erythrolysis nor routine reliable leuko-protection in a single cost-effective hematology analyzer.

For example, the fully automated CELL-DYN® 1600 hematology analyzer performs a simple "soft lyse" categorization of the nucleated leukocytes into roughly lymphocytes, monocytes and neutrophils with the few eosinophils and basophils interdispersed amongst these major lyse-modified leukocytes subpopulations. The CELL-DYN® 1600 uses a one-dimensional impedance transducer whose leukocyte results are totally invalidated by the presence of very numerous lyse-resistant erythrocytes. On these problem samples, neither the intended crude subcategorization of the nucleated leukocytes nor even the total nucleated leukocyte count is obtained under the "soft lysis" conditions. Consequently, laboratories which must process many neonatal blood samples which contain inherently lyse-resistant erythrocytes often have to purchase a second automated hematology analyzer that utilizes a "hard lyse" in order to effectively destroy all of the neonatal erythrocytes. Inevitably, the "hard lyse" also destroys all the cytoplasm of the nucleated leukocytes leaving behind only the virtually identical leukocyte nuclei as a single peak very similar to the E peak of FIG. 1—but sitting at around 66 fl (LEEV). These nuclei can be analyzed to give a correct total count of the nucleated leukocytes, but they no longer permit sub-categorization of these cell types to give a lyse modified but quite useful version of the so-called differential leukocyte profile seen in FIG. 1.

If this "hard lyse" analyzer is the same CELL-DYN® 1600 designed for the "soft lyse" suitable for typical human blood samples, then the quality-assuring algorithms of the instrument sound alarms indicating the profound distortion of the standardized soft-lyse differential leukocyte profiles. Under the guidelines of GLP (Good Laboratory Practices) and CLIA (the Clinical Laboratory Improvement Act)—any alarm conditions on an instrument need individual investigation and attention. In response to this dilemma, the CELL-DYN® company has marketed a slightly modified hematology analyzer, the CELL-DYN® 1300 which can be run effectively on "hard lyse." This slightly less expensive instrument solves only the total leukocyte counting problems—the WBC—associated with hard-to-lyse erythrocytes. However, this is an expensive solution to the customer since an additional instrument occupies space and requires full support even though it has sacrificed all information on leukocytes except the total count of erythrolysis-surviving cytoplasm-free leukocyte nuclei. By comparison with the morphologic leukocyte information available in blood film preparations, no differential or morphologic information is available on the resulting single-peak leukocyte histograms about the subpopulations.

Note specifically that it has not been possible for anyone to find an attractive "intermediate lyse condition"—intermediate in erythrolytic strength between the "soft lyse" of the CELL-DYN® 1600 and the "hard-lyse" of the CELL-DYN® 1300. When an attempt is made to select such lyse conditions, then the partly lysed neutrophils will vicariously migrate into the region of fully stripped nuclei. Under soft-lyse conditions this is the region of the small erythrolysed lymphocytes. This compromises the crude but useful differentiation of the nucleated leukocytes into predominantly stripped lymphocytes [around 66 fl (LEEV) in FIG. 1], slightly lyse damaged neutrophils (more or less where the G granulocytes are in FIG. 1) and moderately damaged monocytes in between the L and N cell residua and identifiably, visibly, flanked by basophil residua and eosinophil residua where these cells are present in significant concentrations in the blood.

Two generations of CELL-DYN® 3000 instruments currently exist. The first generation version, the CELL-DYN® 3000.1 can easily be converted into the second generation CELL-DYN® 3000.2. This second generation CELL-DYN® 3000.2 exploits the present invention. This invention adds the additional dimension of time to the four dimensional optical leukocyte information of the first generation instrument. In order to overcome the problem of hard-to-lyse erythrocytes (making CELL-DYN® 3000 leukocyte counts incorrect and therefore unacceptable), the first generation CELL-DYN® 3000.1 was sold in conjunction with a CELL-DYN® 1300 or 1400 or with a CELL-DYN® 1600 utilizing hard lyse. The second generation CELL-DYN® 3000.2 which will exploit the present invention no longer requires a degraded companion instrument. In fact, the invention which represents the difference between CELL-DYN® 3000.1 and CELL-DYN® 3000.2 has made a much more complex CELL-DYN® 3000 A system redundant in its simplest conception. That CELL-DYN® 3000 A was developed as a combination of a CELL-DYN® 3000.1 and a CELL-DYN® 1300 within a single instrument no larger than the CELL-DYN® 3000.1. The successful alternative represented by the CELL-DYN® 3000.2 is far more cost-effective.

The present invention accommodates the use of strongly erythrolytic agents and conditions to ensure complete erythrolysis because it provides for the precise correction of leukocyte counts to compensate for the leukolysis accompanying the use of strongly erythrolytic agents or conditions. The method of the present invention takes full advantage of the experimentally acquired recognition that a leukocyte population lyses at a calculable, relatively stable and comparatively slow decay rate in the presence of suitably chosen strongly erythrolytic agents or conditions. Those leukocyte decay patterns can be documented over the relatively short time period involved in the leukocyte counting phase, and the resulting decay rates can be used to accurately estimate the concentration of the leukocyte population that was initially present in the sample solution before the leukolytic process began at the commencement of the leukocyte sample processing cycle.

Even though cell count rate monitoring is well known in the industry, it has not been used for this purpose. It is often used to assess the integrity of the detection zone of cell counters, or the stability of the volumetric flow rates of the cell-containing sample solution through the transducer during the counting process. It is also known as a means to insure that the cells under analysis are not adhering to one another as they pass through the detection zone. Monitoring of count rates was used for these purposes during the early evolution of the blood cell counters since MCS (Multi-Count Scaling) capability existed on most multi-channel analyzers produced for the Nuclear Physics field since the 1960's. When these instruments were coupled to the early blood cell counters, monitoring count rates during a cell counting cycle was a simple and automatic procedure. (yon Behrens, W. E. and Lander, Proc. Australian Soc. Med. Research, Vol. 2, p. 380, 1970). Furthermore, the outputs could be readily coupled to a plotter. There was no use of rate information over time to generate quantitative population behavior.

MULTIPLE CHANNEL INSTRUMENTS

Another prior art technique for identifying, categorizing and enumerating cells present in a whole blood sample utilizes separate multiple channel analyses with separate multiple sample volumes in which cell aliquots are subjected to differing, highly specific lysing conditions. In automated instrumentation utilizing this technique, a whole blood sample is divided into a plurality of aliquots. These aliquots are then separately subjected to differing lytic conditions which are chosen to lyse away all cell components in that aliquot except the one cell population of interest. These separate sample aliquots are subsequently processed in parallel in their own channel using their own transducer to gather count information on the surviving unlysed cell populations. This approach has disadvantages because of the hardware and reagent complexity of the instrument that is required to execute the multiple techniques. High manufacturing, maintenance and quality control costs are generally associated with the resultant complex instrumentation and complex reagent systems. Furthermore, the purity of the surviving cell populations is never assured.

One instrument which practices this multiple channel technique is Toa's E8000 ® Analyzer. This instrument employs four channels for cell analysis. Thrombocytes, eosinophils and basophils are counted in their own separate channels. Lymphocytes, neutrophils and monocytes (together with the interdispersed thrombocytes, eosinophils and basophils) are crudely categorized and enumerated in a fourth channel exploiting both DC and AC electrical impedance visualization principles. Erythrocytes are processed with the thrombocytes in the thrombocyte channel without differential lysis. Hemoglobin is processed in an additional channel after maximal, total erythrolysis.

The H1 Hematology Analyzer of Technicon uses only two cell transducers and hemoglobinometer for processing a blood sample differently prepared, but it processes cell aliquots consecutively in these transducers and is at least as complex as the Toa/Sysmex E 8000 ® since it has to use more than ten different reagents.

The CELL-DYN ® 3000.1 A is also such a complex instrument, though in its CELL-DYN ® 3000.2 version it can now offer important new cell classification information.

The present invention provides significant advantage over the prior art multiple channel categorization and enumeration technique. It permits the use of a simpler instrument, necessarily employing only a single channel and a single erythrolytic reagent and process for a powerful multi-dimensional categorization and enumeration of all the nucleated leukocyte subpopulations. The CELL-DYN ® 3000.2 described below utilizes a total of only two transducers and only three simple reagents for processing thrombocytes, erythrocytes, hemoglobin and all the leukocyte subpopulations.

SUMMARY OF THE INVENTION

The method of the present invention enables recognition of the presence of unstable, diluted cell populations which are losing their integrity in what can now be formally recognized as a regular manner. It enables categorization with actual enumeration and a more refined characterization of these cell populations. According to the present method, a specific cell population survivorship rate is interrogated and monitored after the cell suspension conditions are adjusted. All the suspended cell populations are examined or tracked during the short time interval—the cell counting phase of the sample analysis cycle—during which cell counting pulses are acquired. The cells are examined either in the region (or native state) they occupy when substantially intact (which sometimes means alive) or in their degraded state as ghosts, bare nuclei or dead cells. The transition of any given single cell between these states is sudden and saltatory since it is extremely difficult to arrange conditions in which cells are perceived in transit between the two states. The cells may also be monitored in both states independently but simultaneously. The transition rate (from the intact state to the degraded state) of any or all of the monitored cell populations enables useful flagging, provides sensitive identification and characterization information and yields correct enumeration data.

In preferred embodiments of the present method, the interrogated and monitored cell population response is either the decay rate of the intact cell population or the genesis rate of the degraded or ghost cell residuum. This response information can be used to establish when or if major destructive cytoplasmic lysis of a cell population has occurred or is still occurring. This information can then be used to identify, to categorize and to characterize certain abnormal cell populations. The observed cell population transition rate can also help to accurately enumerate specific cell populations by accounting exactly for the extent of cell population degradation transpiring during the handling and measuring of the cell suspension. This degradation is caused by the continuous lytic process which begins in an instrument prior to the actual counting of the cell population.

A particularly preferred embodiment of the present invention is applied to whole blood samples and leukocyte enumeration. Cost-effective, strong erythrolytic conditions are employed to ensure complete erythrolysis thereby eliminating the adverse effect of interfering erythrocytes on the leukocyte counts. Any leukolysis resulting from the strongly erythrolytic conditions is identified, characterized and quantified by interrogating and monitoring the count of the lysis-surviving cells over time. The mere fact of leukolysis can be used to sense the presence of lyse-sensitive leukocytes and to indicate thereby that most of the other leukocyte counting technologies will tend to underestimate the correct total and partial leukocyte counts. The rate of leukolysis is employed to adjust degraded leukocyte counts which result from inadvertent leukolysis.

A particularly preferred method is advantageously practiced on a flow cytometric instrument capable of five sub-population differentiation of the nucleated leukocytes utilizing two forward and two orthogonal light scattering dimensions to detect, categorize and count the nucleated leukocytes. With efficient total erythrolysis and the new exploitation of the dimension of time, this same analytical pass can also be used to evaluate the anucleate lyse-surviving mammalian thrombocytes.

BRIEF DESCRIPTION OF THE FIGURES

FIG. 2 is an integrating log-log diagram of the same information contained in the two separate recorded cell population views of FIG. 4.

FIG. 5 shows two, one-dimensional views of transitional post-lytic and pro-lytic erythrocyte population data acquired simultaneously in the impedance transducer used in FIG. 4.

FIG. 6B is an attempt to show on these two-dimensional projections the four-dimensional regions in which the five intact subpopulations of nucleated leukocytes are tracked in five dimensions. L=lymphocytes, M=monocytes, Ne =Neutrophils, Eo=Eosinophils, Ba=Basophils, R=Residua and T=large Thrombocyte aggregates and artifactual pulses from such structures as chybomicra which are "Thresholded out" of the total leukocyte count or WBC.

FIG. 11A shows four different samples containing hard-to-lyse neonatal erythrocytes.

FIG. 11B shows counts versus time for five blood samples from patients with chronic lymphocytic leukemia in various stages of therapy. Only two of the counting phases have been extended into the forced recount mode for operating any CELL-DYN® 3000.

FIG. 11C shows counts versus time for two different adult patients exhibiting hemoglobinopathies. Note the much higher resolution used for the ordinate axis.

DETAILED DESCRIPTION OF THE INVENTION

DEFINITIONS

Figure 1:
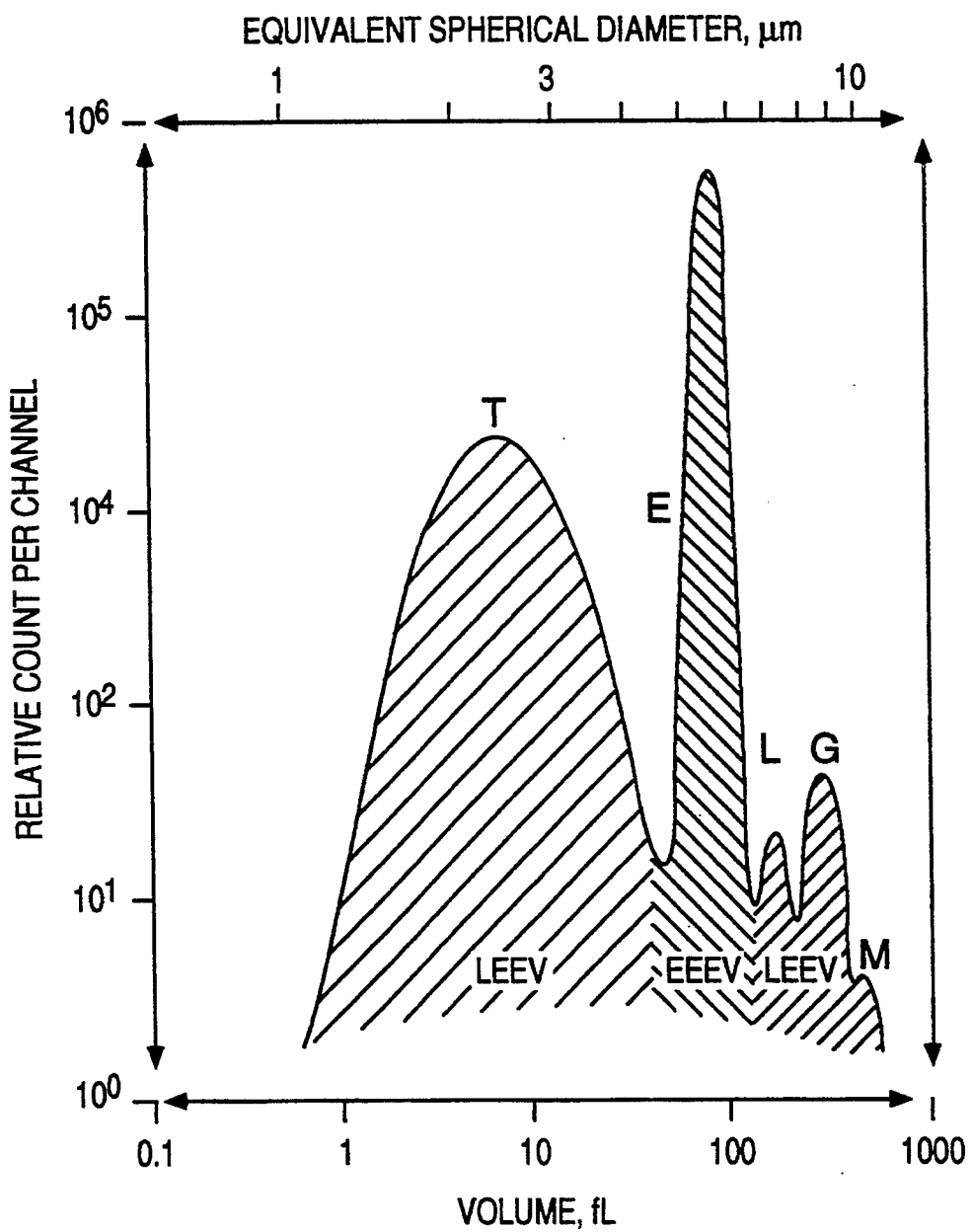
FIG. 1 is a log-log plot of one-dimensional impedance data generated in 1973 on isotonically diluted whole blood with a hydrodynamically focussed research blood cell analyzer. T=thrombocytes or platelets, E=erythrocytes or red cells, L=lymphocytes or small mononuclear cells, G=granulocytes or polymorphonuclear cells, and M=monocytes or large mononuclear cells.

A number of terms are used throughout the specification and claims which may have special meanings or slightly different connotations in the context of this invention. Therefore these terms will be defined in this section.

"Cell population," as used throughout, refers to a clonally homogeneous population of the same cell type. Thrombocytes are homogeneous in this sense as are populations of fragile lymphocytes and of monoclonally identifiable lymphocyte such as the subset of T-cells. Erythrocytes are also clonally homogeneous in this sense even though cohorts of different ages may have left the bone marrow over 120 days apart and therefore do exhibit age-related differences.

In the present discussion, all of the blood cell populations other than the erythrocytes will be referred to as subpopulations of the broad group of leukocyte populations since thrombocytes, lymphocytes, monocytes, neutrophils, eosinophils and basophils have considerable similarity in cytoplasmic structure. For example, upon centrifugation of blood, all these cells accumulate in the white buffy coat layer above the red cells (see U.S. Pat. No. 3,914,985). Similarly, all these populations of FIG. 1 tend to resist the hypotonic and analogous lysis which easily destroys all the erythrocytes of FIG. 1. Despite such superficial similarities amongst all the leukocytes as opposed to the erythrocytes, it is a central tenet of this invention that each homogeneous cell population will have its own unique response pattern. Therefore, even though we have adopted this simplified nomenclature, it is fundamental that each of these leukocyte subpopulation cell lines behaves as an autonomous, distinct population. The shared characteristics of the leukocyte subpopulations merely distinguish them as a whole from the numerically dominant erythrocyte population.

The term "sample solution" is intended to refer to a liquid sample. This term does not imply that the intact cells or the lysis-generated cell carcasses are suspended in a solution in any particular way, or that a biological sample—such as blood or urine—has to be diluted or pretreated before practice of the claimed method. Sample solution therefore is intended to cover both undiluted body fluids (e.g., whole blood, semen, etc.), as well as liquid samples which have been diluted, preserved, treated, etc. It also includes diverse suspensions and cell cultures including suspensions of plant cells. When a particular sample solution condition is required by the methodology, the condition will be explicitly recited herein.

The term "kinetic lysis" is used here to characterize a cell population's response phenomenon in which cell lysis of very major proportions takes place at a progressive rate in the various cell cohorts comprising the population. "Kinetic lysis or decay" is intended to convey that, over time, there is a continuum of disappearance of intact cells or appearance of cell remnants in identification regions in which it has traditionally been assumed that count rates are stable during acquisition of cell count information.

"Cell count per unit volume of sample" is used to refer to the type of enumeration data obtained according to the method of the present invention. For purposes of clarity, it is to be well understood that the enumerating means typically performs a count of the detectable number of cellular events passing through the interrogated portion of the field of view of a detector. This raw data information is segmented in time to create a count of cellular events per analyzed volume per unit of time. Since commonly available enumerating means often require substantial dilution of the original sample solution to permit cell by cell flow through the detector, the raw enumeration information is related back to a unit volume of the original sample solution in order for the enumeration information to be clinically valuable. Therefore, the actual enumeration data is processed to account for any dilutions or reagent additions in order to provide a cell count per unit volume of the original sample solution. Thus, the scope of the present invention encompasses any method to provide cell counts and cell identification which utilizes the enumeration data based upon normally stable quantitative information on intact cells.

"Cytolysis" occurs when the conditions under which a cell is maintained cause the cell to exceed its cytolytic threshold. That threshold is a physico-chemical function of the cell's macro and microenvironments. Consequently, cytolysis occurs when the cell is deliberately exposed to solutions or environments characterized by physico-chemical conditions which result in the cell exceeding its cytolytic threshold. The degree to which the members of the cell population undergo cytolysis during the counting phase of the instrumental cell analysis cycle—and the rate at which cytolysis takes place—provide useful information for identifying the presence of certain cell types, for the existence of abnormalities in certain cell types, and for accurately enumerating the initial number of cells within an interrogated cell population that is observed to be undergoing progressive kinetic lysis.

Innumerable purely physico-chemical conditions which lead to cytolysis are known in the art. It is known that solution ionic strength, pH and osmotic and oncotic pressure create conditions enhancing cell preservation or leading up to cell lysis. Additionally, temperature has a strong effect on the rate of cytolysis. In the present specification, this traditional understanding of physico-chemical conditions responsible for cytolysis is expanded to also include solution handling conditions which may exist in automated counting instruments causing inadvertent cytolysis. These conditions may include steady vigorous mixing or constant turbulence or shear stress present in the fluid portions of the instrument (e.g., as described in U.S. Pat. No. 3,071,770). Additionally, there are known cell membrane injuring and cell membrane modifying lytic agents which are cytolytic to specific cell types (e.g., U.S. Pat. No. 4,962,038; European Patent Application No. 444,241). Other agents and conditions are known to those of ordinary skill in the art.

Cell population response, cytolysis and cell counting are here explicitly related to the concept of first order or direct cell visibility in the present state of the art instruments. This "direct cell visibility" can be contrasted with the indirect detection of the response of a cell population to a specific interrogation. This second order cell detection clearly distinguishes the present invention over the related prior art. Additionally, when a cell counting technique is chosen for a particular cell suspension, the cell counting event of indirect detection occurs under a particular set of conditions leading to a directly measurable signal. For example, in measurement of cells by electrical impedance, certain cell suspension conditions and electronic signal conditions are employed to create measurable signals indicative of the presence of certain cells in the cell suspension. A "window of observation" is chosen based upon previously observed responses, and the counting event is normally conducted within this window.

The previously inadvertent (but now manageable) cell population response to the lytic solution conditions and to the prevailing electronic signal inducing conditions may now be modified systematically by changes in the solution condition or signal conditions. When the lytic response of a cell occurs, the potential signal generated by the cell carcass or ghost may be moved out of the original window of observation such that the monitored population has become totally invisible and therefore ceases to exist in the original window of observation. In fact, the response of an intact cell population does disappear from one locus as it undergoes lysis but a response from the resulting cell carcass, residuum or ghost may appear in a quite distant locus. In this way, in addition to "visualizing" or measuring the disappearance or decay of a cell population in response to an imposed condition, it is also possible to "visualize" or measure the appearance of cell residua in another window of observation. Thus, the monitored "decay" rate in any given region may actually even be positive. One mechanism accounting for such a positive decay rate implies a local increase in cell residua and a distant decrease in the number of intact cells. Another mechanism implies a major change within the cells—such as the precipitation of granules or of internal sol membrane constituents into energy transducing gel membranes—with transition of previously undetectable cells into suddenly visible cells.

Figure 12A:
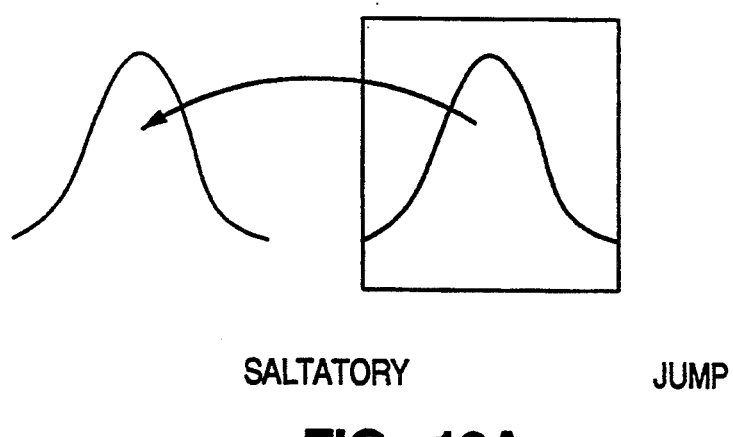
FIGS. 12A and 12B are pictorial representations of conceptual ideas illustrated by this invention.
Figure 12B:
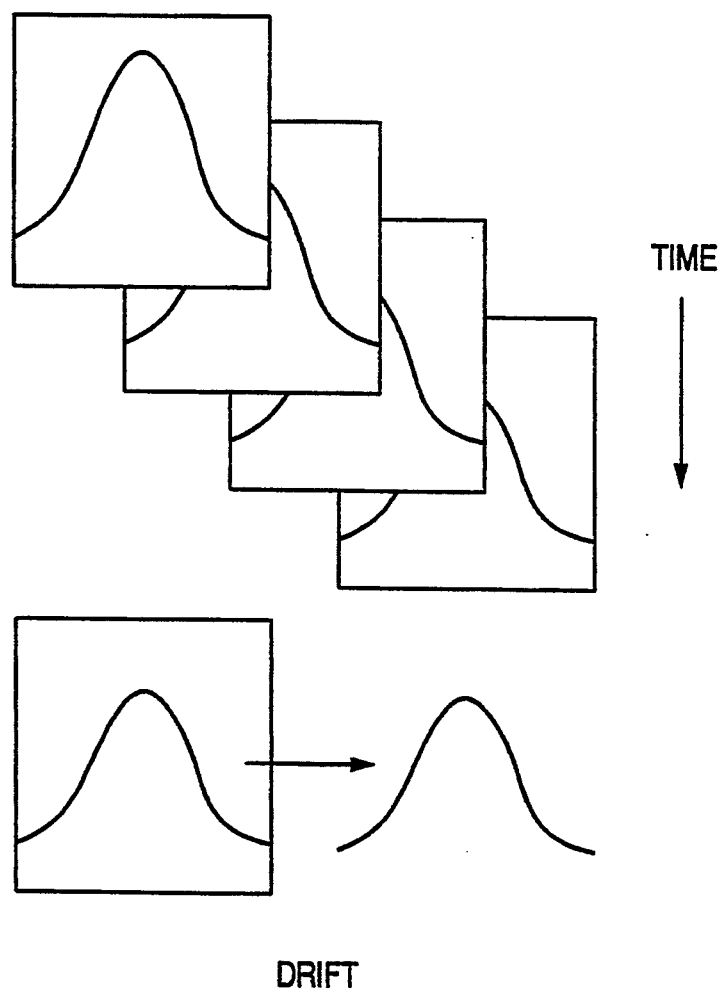

We illustrate this concept of saltatory changes in relative visibility with readily depicted one-dimensional impedance data generated on an erythrocyte population undergoing kinetic lysis during erythrocyte fragility testing. FIGS. 12A and 12B illustrate the concepts of saltatory and drift with respect to the concepts of the present invention. To communicate the various ideas presented, the content of FIGS. 1 to 3 and of FIGS. 4 and 5 will now be developed. The log-log data of FIGS. 1 and 3 were generated in the 1970's with a hydrodynamically focused research blood cell analyzer described in Clinical Research, 1974, 22, page 123A. The data of FIGS. 4 and 5 were generated with one of the erythrocyte/thrombocyte impedance transducers used in the CELL-DYN ® instrument line from the CELL-DYN ® 900 to the CELL-DYN ® 3000. These impedance transducers do not employ hydrodynamic front focussing; and the clinical data presentations are linear. However, the basic visibility phenomena are otherwise comparable in the 1970's research instrument and in the clinical CELL-DYN ® instruments of the 1980's and 1990's.

FIG. 1 shows all of the blood cells that are visible by impedance sensing in diluted, anticoagulated whole blood. The letters in FIG. 1 stand for the frequency distributions of Thrombocytes (T), Erythrocytes (E), Lymphocytes (L), granulocytes (G: neutrophils, eosinophils and basophils) and Monocytes (M).

Figure 4A:
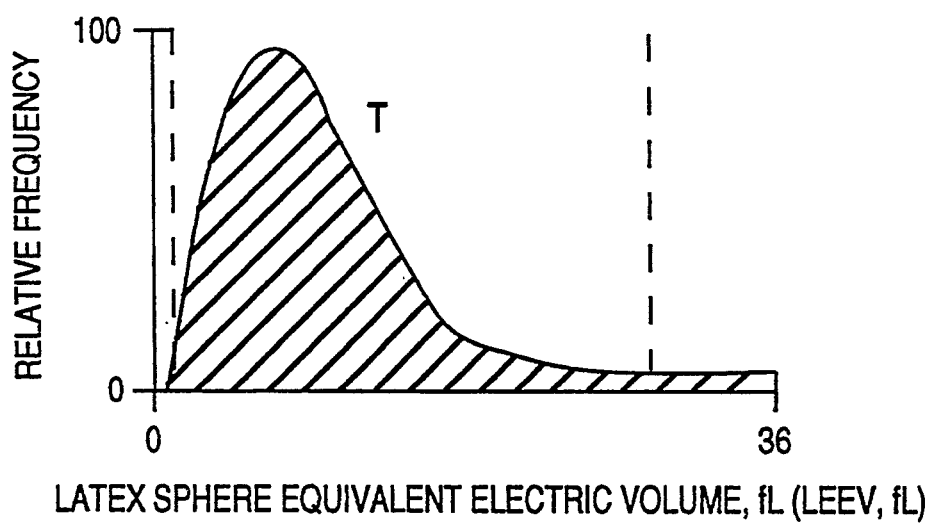
FIGS. 4A and 4B show two, one-dimensional histograms of the thrombocyte (platelet) and erythrocyte (red cell) population data acquired simultaneously on diluted whole blood with the von Behrens plate impedance transducer used in the CELL-DYN® 3000, CELL-DYN® 1600 and CELL-DYN® 1300. The field-error distorted erythrocytes, $E_F$, arise because this transducer uses only passive rear focussing—not front focussing. These thrombocytes and erythrocytes are not lysed prior to analysis.

By convention, spherical latex particles of known volume are used to calibrate impedance size histograms for EDTA-sphered thrombocytes (FIGS. 1 and 4A). These particles are also used to calibrate impedance size histograms for the relatively rigid spherical leukocytes (FIG. 1; L, G and M). This yields abscissa calibration in Latex Equivalent Electric Volume femtoliters (or LEEV fl) for these cells (von Behrens, 1975 Mediterranean Macrothrombocytopenia. Blood 45:199). These LEEV calibrated profiles are shaded darker in FIG. 1.

Such latex spheres are also used to crudely calibrate impedance size histograms for erythrocytes. However, because of the non-spheroidal form of erythrocytes, because of erythrocyte deformability, and, above all, because of the sensitive volume response of erythrocytes to the physico-chemical variables listed earlier, a complex shape factor must be used to refine this crude latex calibration at the clinical level. This shape factor adjustment implicitly includes a form factor, a shrinkage or swelling factor and an electrical field error term. However, this shape factor is not usually computed explicitly. Instead, the hematology analyzers are calibrated directly in EEEV fl or Erythrocyte Equivalent Electric Volume femtoliters. Establishment of this exact scale is discussed later under the heading of the thrombocyte and erythrocyte population parameters of the CELL-DYN ® 3000 instrument line.

In many hematology analyzers the EEEV fl differ by a factor of around 1.5 from the LEEV fl (von Behrens 1975 loc. cit.). This means that, if the thrombocytes visible in FIG. 4B and FIG. 1 were reported out in EEEV, then they would appear to be 1.5 fold larger in volumetric size. This shift is apparent in FIG. 2 which is a log-log representation of the data of FIGS. 4A and 4B.

The lightly shaded erythrocyte profile of FIG. 1 was actually moved to the right by a factor of 1.5 from its original pulse location so that the lower abscissa now represents generic spherical volumes and the upper abscissa represents generic spherical diameters. Thereby the erythrocytes are represented in EEEV.

In order to acquire sufficient nucleated leukocytes (i.e., L, G and M) to illustrate an actual distribution for the 2,500 lymphocytes/$\mu$l and 3,100 granulocytes/$\mu$l of FIG. 1 we had to process 6.1 million erythrocytes and 187,000 thrombocytes. This process took 46 minutes.

As emphasized above, because of "the need for speed," commercial hematology analyzers tend to process erythrocytes, thrombocyte and nucleated leukocytes separately—each in its own window centered roughly on the peaks of the log-log profiles of FIG. 1.

Figure 2:
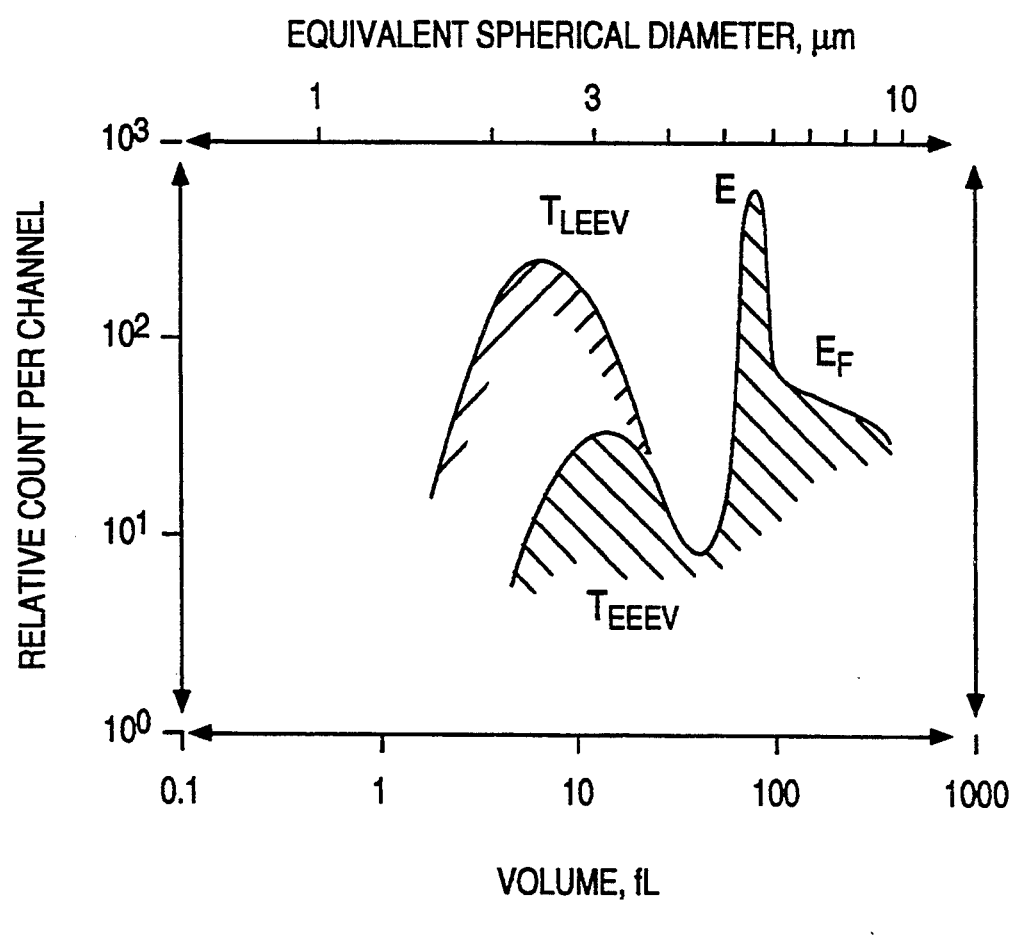
Figure 4B:
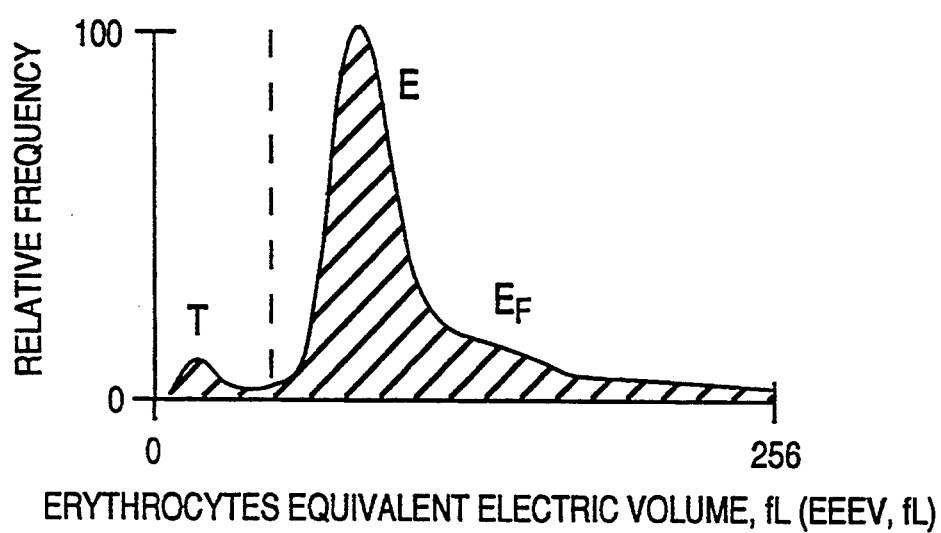

For example, we can look at the erythrocytes as shown in FIGS. 2 and 4B. As already noted, FIG. 2 is actually not raw data but rather the log-log re-presentation of the raw data of FIG. 4A (thrombocytes; darker profile in FIG. 2) and FIG. 4B (erythrocytes; lighter profile in FIG. 2 with the numerically infrequent thrombocytes of FIG. 4B also shown).

FIG. 4 shows two volume histograms for cell data acquired on the clinical CELL-DYN ® 3000.1 impedance transducer. FIG. 4A shows the thrombocytes (platelets) and FIG. 4B shows the erythrocytes (red cells) which were counted during the routine counting cycle. The dotted vertical lines in both figures represent the counting boundaries (or windows of convenient observation) for the different cell populations. Contrasting the two histograms in FIG. 4, the region below the dotted vertical line of the erythrocyte histogram (4B) shows a small frequency of thrombocytes. The platelet histogram (4A) reports information about the same thrombocyte population shown in the left hand region of the erythrocyte histogram (4B). However, the data in FIG. 4A represent the much smaller window of observation. Besides the difference in calibration units (i.e. LEEV versus EEEV), the two histograms of FIG. 4 differ greatly in the dynamic range of their abscissa. Contrast the expanded window for the erythrocyte histogram with a window approximately five times narrower for the thrombocyte histogram.

The right shoulder of the erythrocyte peak (marked $E_F$ in FIGS. 2 and 4A) is an instrument artifact known as the field-error function (von Behrens and Edmondson; J. Histochen, Cytochem 24 247–256 1976). This erythrocyte generated shoulder seen in unfocused impedance systems would quite obscure the lymphocytes, granulocytes and monocytes present in the diluted whole blood of FIG. 1 even if these leukocytes were present in higher concentrations. Clearly, if the dominating erythrocyte population of FIG. 1 can be simply lysed away (so that it totally disappears from view), then the infrequent thrombocytes and the literally rare nucleated leukocytes shown in that log-log figure become accessible to convenient and cost-effective rapid analytical processing.

There are erythrolytic agents (such as the saponins) which do permit total erythrolysis without perceptible residual erythrocyte ghosts. However, to develop the concept of direct cell visibility and indirect cell detection, it is preferable to change the observable response of the erythrocytes using blood dilution with a hypotonic solution. This makes erythrocytes expand in volume, and become prolytic spheres having the same membrane surface area as the original circulating biconcave erythrocyte discs. Under incrementally more intense hypotonicity, the erythrocyte will suddenly seem to "disappear" or to become "invisible" electrically in its original window of FIG. 4B. There is a saltatory change in cell visibility because the membrane has suddenly become porous to the electric current and to the solution of hemoglobin molecules which comprises the erythrocyte cytoplasm. The pro-lytic erythrocyte spheres suddenly become postlytic erythrocyte ghosts. The current now passes substantially through the cell rather than around it. However, as shown in FIGS. 5A and 3, erythrocyte ghosts or stroma structures do give signals, albeit many-fold smaller in electrical size than the signals from erythrocytes under the standard observation conditions which are used to generate traditional clinical erythrocyte volume and count information.

Figure 3:
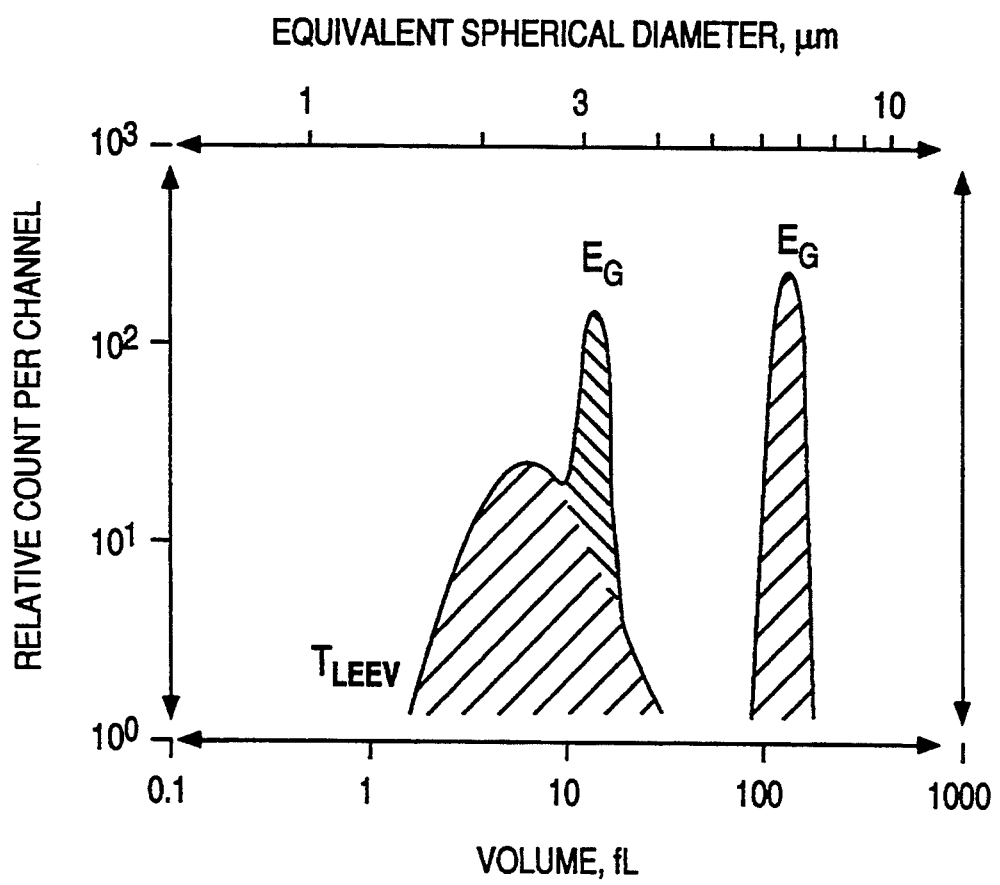
FIG. 3 is a log-log plot of one-dimensional impedance data generated in 1976 on hypotonically diluted whole blood to generate a mixed population of pro-lytic and post-lytic erythrocytes in the manner also illustrated in FIG. 5.
Figure 5A:
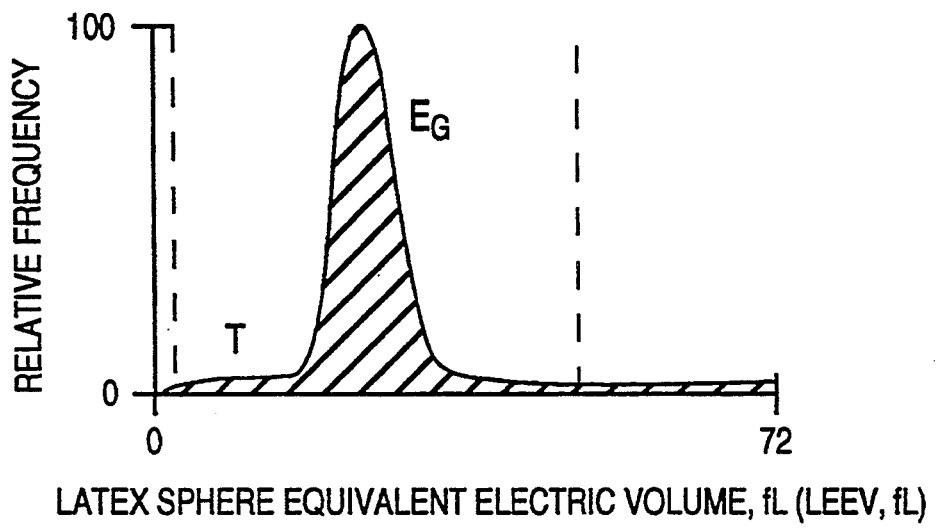
FIG. 5A depicts post-lytic erythrocytic ghosts and virtually unaffected thrombocytes.

During the counting process the signal for erythrocyte ghosts can appear suddenly in the platelet size region as shown in FIGS. 5A and 3.

Figure 5B:
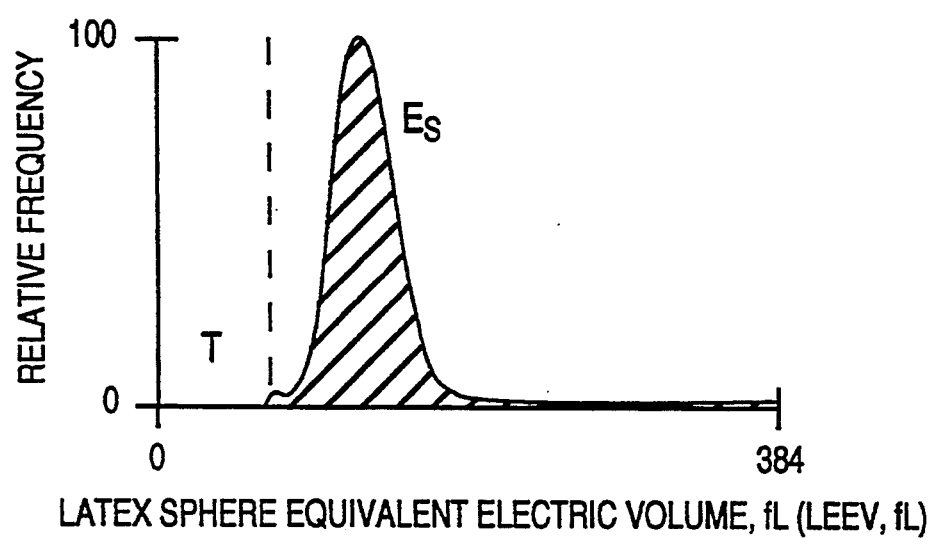
FIG. 5B depicts pro-lytic erythrocytic spherocytes. These patterns are obtained when blood is analyzed under gentle erythrolytic conditions arrived at by dilution of whole blood into hypotonic saline solution.

The histogram of prolytic erythrocyte spheres (FIG. 5B) shows data for the range of 0 to 384 "gated out" fl[LEEV]. A small population of thrombocytes is "gated out" of the region of observation to the left of the dotted vertical line in FIG. 5B. In FIG. 5A, this "thrombocyte region" of FIG. 5B is the region of interest; and it is now scaled with higher amplification and thereby resolution. It is now seen to be dominated by erythrocytes ghosts. The presentation of FIG. 3 reveals the composite nature of the cell populations in the expected thrombocyte region. In the linear ordinate presentation of FIG. 5A, the thrombocyte population is almost overlooked. The logarithmic ordinate presentation of FIG. 3 clearly reveals it. However, as used here, the thrombocytes were clearly visible in FIG. 5A. They had been seen and registered by the transducer and circuit. On the other hand, the erythrocyte ghosts of FIG. 5A were invinsibile in FIG. 5B. The cells had undergone a saltatory translocation or transition in location. This dominant population of erythrocyte ghosts has begun to appear in the classical thrombocyte region because of the lysing effect of the hypotonic condition on the erythrocytes.

Actually with an instrument similar to that used in FIGS. 1 and 3, all the cell structures in FIG. 3 can be counted simultaneously despite the saltatory erythrocyte translocation. It is obvious to those skilled in the art that under those observation conditions the average cell size of the total observed heterogenous populations will decrease continuously whenever the decay rate taught by the present invention differs significantly from zero. This monitoring of specified mean pulse sizes over the wide dynamic range of the saltatory lytic cell degradation is merely another form of indirect or second order cell visibility change.

This concept of visibility will now be extended from the didactic one-dimensional setting to multi-dimensional feature space.

Figure 6:
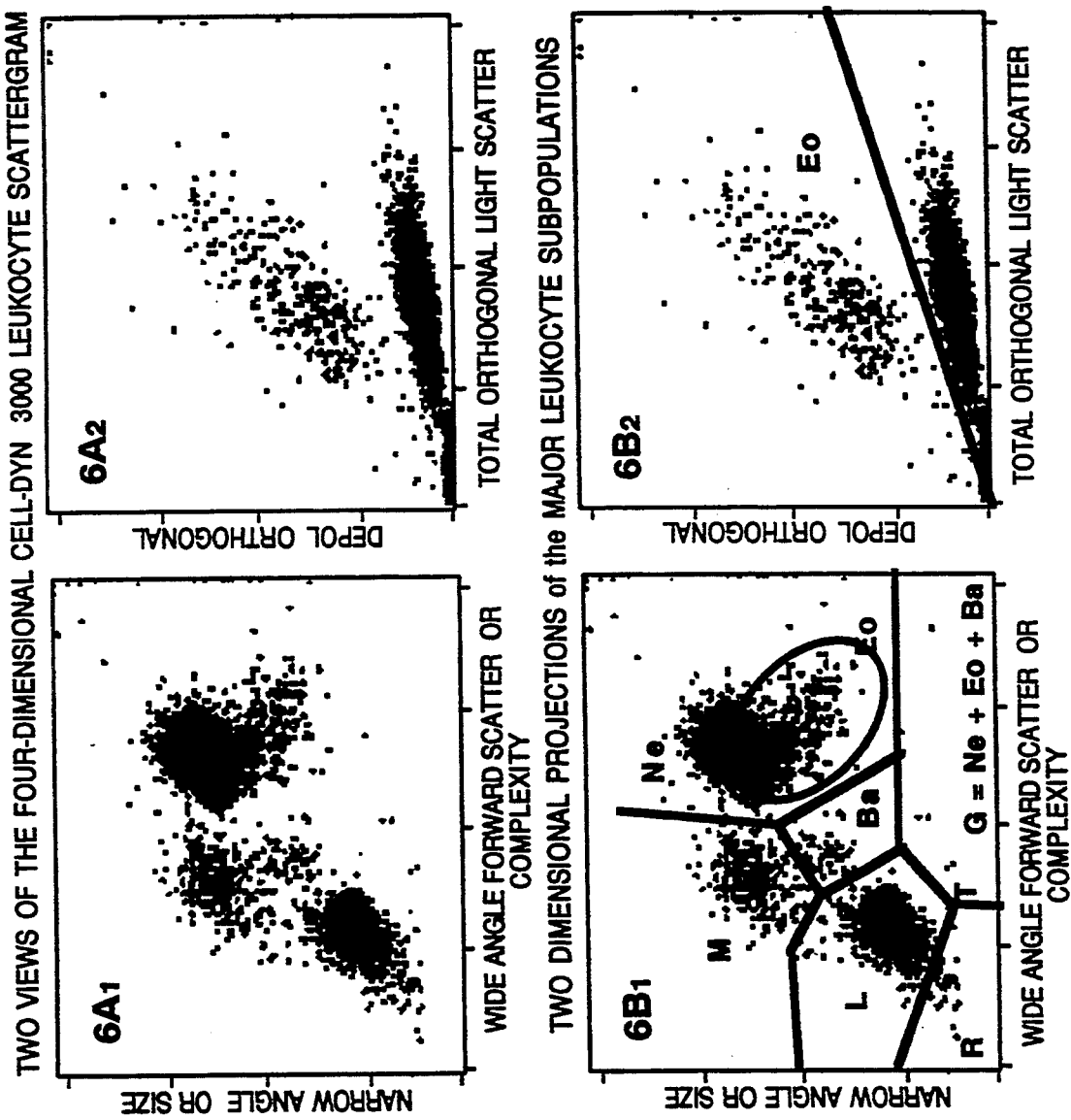
FIGS. 6A and 6B show the same pair of two-dimensional projections FIG. $6A_1$, FIG. $6A_2$, and FIG. $6B_1$ and $6B_2$ representing a set of four-dimensional CELL-DYN® 3000.2 data for the nucleated leukocytes of a whole blood sample from a normal human subject.
Figure 6A:
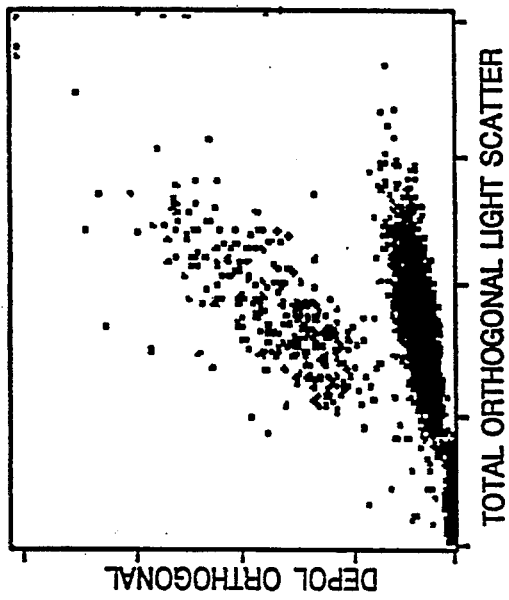
Figure 6B:
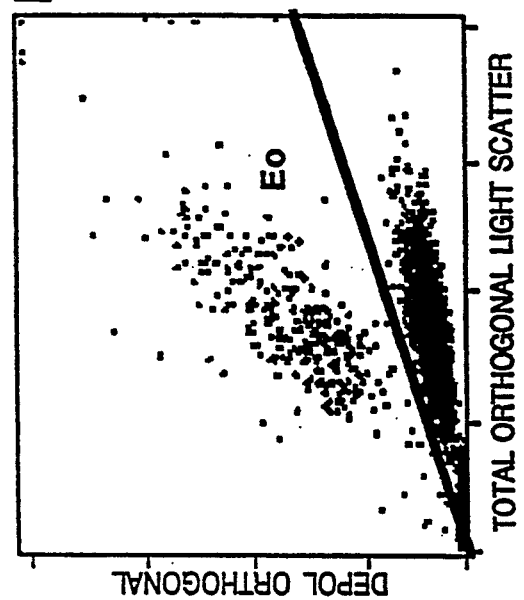
Figure 6C:
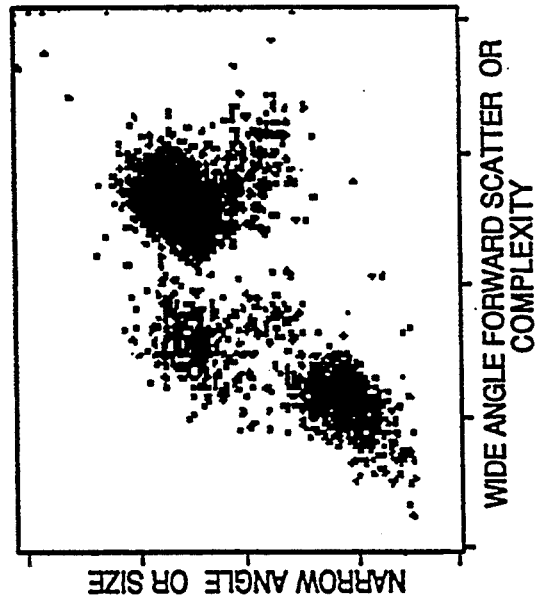
Figure 6D:
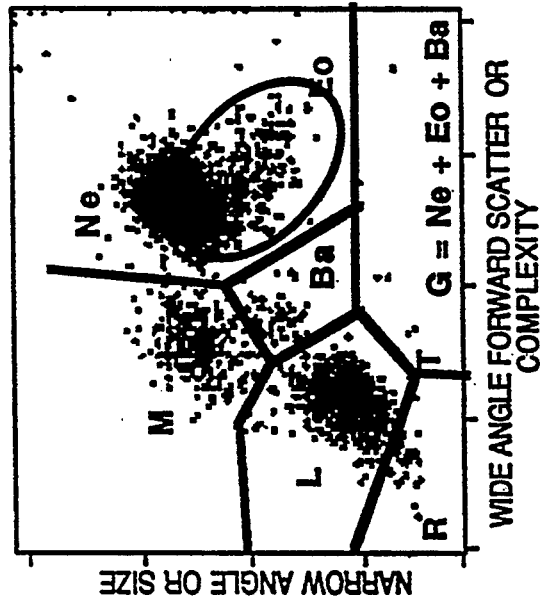

FIG. 6A depicts two different two-dimensional projections FIGS. 6A$_1$ and 6A$_2$ representing the same four-dimensional data for the nucleated leukocytes of a whole blood sample. These data were obtained from a CELL-DYN® 3000.2. FIG. 6B (FIGS. 6B$_1$ and 6B$_2$) depicts these same projections with lines drawn in to provide a rough two-dimensional indication of the five regions in which the subpopulations of intact, nucleated leukocytes are tracked in four-dimensional space throughout the counting phase of the instrument. Region L is where the lymphocytes are found. Region N contains the neutrophils. The monocytes are found in region M. Region Eo contains the eosinophils. The basophils are found in region Ba. Large thrombocyte aggregates and chylomicra may appear in region T, but are not included in the total for lyse-surviving blood cell structures.

Region R is identified on FIG. 6B as an area in which negligible data was obtained for this sample. Under these analytic conditions, the nucleated leukocytes are not visualized in this region. According to the methods taught by the present invention, the appearance of leukocyte residua, ghosts or nuclei in regions where they are normally not seen (e.g., as in region R) can be used to measure a specific cell population's response to imposed conditions. The rate of appearance of cell residua, cell ghosts or cell nuclei in a given region is a parameter which can be used to identify, characterize, categorize and enumerate the number of cells originally present in the sample at time zero of processing, i.e., before the imposition of conditions to obtain a measurable response.

MONITORED CELL RESPONSE RATE

In its broadest conception, the present invention provides a way to identify and to count cells in one cell population independent of other cell populations or inert monitoring particles present in the same sample solution. The present method is capable of identifying, characterizing, categorizing and enumerating cells within a cell population by monitoring the survivorship characteristics of the different cell populations. These characteristics can then be used to develop quantitative and qualitative information about the cell populations originally present in the sample solution before conditions were imposed on the sample to elicit a measurable response. The monitored cell survivorship response may be either the direct disappearance of intact cells as in FIG. 5B or the appearance of cell structures, carcasses, ghosts or residuum as in FIG. 5A (i.e. indirect disappearance of intact cells).

The present method can be advantageously applied to the measurement and characterization of erythrocyte fragility. The monitoring of erythrocyte counts over time during a cytolytic process provides both quantitative and qualitative information about the subject erythrocyte population which may be useful in diagnosis and in following disease therapies.

The use of the present method to evaluate and to characterize erythrocyte fragility is substantially different than prior art techniques which use multiple dilutions to achieve the same result. See, e.g., U.S. Pat. No. 4,040,742 and U.S. Pat. No. 3,606,539. The present method allows such a determination to be made at a single tonicity.

In another embodiment of the present invention, there is a first cell population present in the sample solution which first population can always be made to rapidly exhibit total cytolysis when the cytolytic threshold for that cell type has been greatly exceeded by the addition of a specific lysing agent or by changing the physico-chemical conditions of the sample solution. After cytolysis, this first cell population is thereby reliably rendered invisible to the cell counting mechanism in the region for intact cells of this type. A second cell population present in the same sample solution with a more complex or differing cytoplasmic structure than the first cell population does not exhibit the same very rapid total cell lysis under these conditions but undergoes progressive, slow (kinetic) lysing. For example, most cell types other than erythrocytes (and other than the similarly structured cell vacuoles) are less prone to lysis than these so-called "minimum cytes" because redundant internalized cell membrane can be progressively externalized as the cell tends to expand through extensive hydration. The fact that this second cell population exhibits lysis at all in the relevant time frame, and the rate at which this lysing of the second cell population occurs, are both monitored by taking counts of intact second cell population cells, ghost cells or both. Counts are made over a minimum of at least two different temporally spaced intervals of time commencing after the physico-chemical adjustment of the sample solution causing complete cytolysis of the first cell population.

The information obtained in monitoring the response or decay rate of the second cell population is then used to characterize the presence of decaying cells in the second cell population and to more specifically identify the affected cell populations. This information is also used to accurately estimate the number of intact cells per unit volume initially present in the second cell population by correcting for any inadvertent second cell population lysis which occurred between the time point at which physico-chemical adjustment of the sample solution to lyse the first cell population took place and the commencement of the actual counting phase of the analytical cycle. This temporal correction for inadvertent, specific lysis of the second cell population substantially improves the accuracy of the count for the second cell population. This doesn't merely enhance the clinical value of the count information for the second cell population: it may actually enable the very possibility of any meaningful count on the second cell population.

In another embodiment, the present method is applied to a sample solution containing at least two populations which both exhibit the relevant progressive saltatory kinetic lysis. Each cell in each population undergoes the large change in visibility suddenly, but the entire populations do not lyse almost instantaneously. Lysis occurs at differing lyse or decay rates in response to adjustments in the physico-chemical conditions extant in the sample solution. So-called multicompartment or population specific monitoring of the decay rates and/or of the cell residuum genesis rates provides the readily applied useful information.

When the saltatory populations are cells then this methodology is applicable because simple dilution of the sample solution can create the desirable cytolytic conditions for one or more cell populations. This methodology is also applicable when the sample handling conditions extant in the automated counting system inadvertently lead to kinetic saltatory cytolysis. The method is also applicable to situations in which a lytic agent is added to the sample solution to commence progressive kinetic lysis of one or more populations. The progressive kinetic lysis of the respective cell populations is monitored by acquiring all the data over various time intervals after the commencement of lysis. Generation of cell-population-specific counts of the lyse-surviving cells enables exploitation of population specific decay patterns to quantify certain qualities of the specific cell populations. These patterns range from a decay rate of zero (or insignificant) to a very large and clinically highly significant rate. Such rates and patterns may even be pathognomonic for certain disorders. The specific cell population count monitoring data is further used to correctly categorize and to accurately estimate the number of cells in each cell population which was originally present in the sample solution prior to the time when the sample solution was adjusted to commence cytolysis.

The method of the present invention can be advantageously applied to differential cell analysis of physiologic fluids such as bone marrow, whole blood, blood plasma, cerebrospinal fluid, joint fluid, semen, and organ cell suspensions. It may also be applied to other heterogeneous cell suspensions such as plant cell cultures suspended in medium, plant vacuoles in a suspension with nucleated plant cell structures and enrichments of the organisms in the oceans. The present invention is useful in systems which employ lytic cell population reduction and immediate measurement within minutes. It is not intended to cover methods which employ hours of incubation or culture after lysis to induce a differential cell population response in the form of subsequent growth of lysis-surviving neoplastic cells. The present invention is not intended to cover methods for lysing blood cells in microbiology in order to subsequently culture bacteria that are present.

THE ERYTHROCYTE LEUKOCYTE SYSTEM

In a preferred embodiment, the present invention is advantageously applied to the categorization, characterization and enumeration of leukocyte subpopulations present in whole blood samples. As noted above, the erythrocyte leukocyte system has been extensively studied, and in particular, methods which employ total erythrolysis to process leukocytes have been known.

Every erythrolytic diluent is also leukolytic to some degree, especially when erythrolytic conditions are strong. Eventually, the cells of a given leukocyte population will exceed their specific hemolytic threshold one at a time. If the cell counting system is set up to register the presence of the expected intact leukocytes, each disintegrating cell within a homogeneous leukocyte subpopulation is lost as a result of its invisibility in the usual region of the counting system. These leukocyte cells reach their hemolytic threshold essentially one at a time because they exhibit differential behavior or differing maturity with respect to lytic sensitivity. Some members of the subpopulation are far more sensitive than the typical or median cell representing the population. Others are far less sensitive. The important characteristic of these leukocyte populations is that, as they undergo the process of lysis any specific population will exhibit a continuum of intact cell loss or cell carcass genesis over a prolonged time which is measurable and can be used to document the important specific rate information which characterizes this continuous decay or genesis process for this specific population under the employed specific cytolytic conditions. This specific rate information can be used to correctly enumerate and to categorize the originally present intact cell population. This specific rate information can also serve to characterize previously unmeasurable properties of the cell population which are clinically important in disease classification and thereby in patient therapy and patient follow-up.

For example, in samples which are said to contain a subpopulation of cells with many fragile cells, this continuous kinetic differential behavior of the different cohorts comprising the entire cell population with fragile cells is preserved. In other words, the entire subpopulation has an altered specific behavior pattern, not just the apparently fragile members perceived under the microscope. These fragile cells are like the visible tip of an iceberg. There is always "more to it than meets the eye." Similarly, there is a homogeneity to the atypicality or perceived heterogeneity of the sensitive subpopulations. This homogeneity is analogous to the blood cell population homogeneity studied by one of the inventors for many years, for example, Homogeneous Heterogeneity of Platelet Populations, W. E. von Behrens, Proc. Aust. Soc. Med. Res. 2:339, 1970. However, it is here exploited for the first time, as a life or death, all or nothing, kinetic saltatory phenomenon during the difficult process of reliable cell counting. Every cohort of the affected subpopulation cell clone is more sensitive to lysis than corresponding cohorts from lyse-resistant or unaffected cell clones or typical leukocytes. This is the physical interpretation of a single homogeneous decay rate parameter for a clonal population. Therefore, complete erythrolysis of these blood samples can even be effected while the fragile leukocyte subpopulation undergoes progressive kinetic lysis during the signal generation phase from which the leukocyte counts are derived by the analyzer. (The time for disappearance of the iceberg in warm equatorial water is merely proportional to the size of the visible tip; this disappearance time is much longer than the time it takes to melt the original tip!) The population cell count data at two or more points in time during the progressive lysis of any of the categorizable homogeneous populations is captured to generate a mathematical representation of the population decay or cell carcass genesis.

On the one hand, this mathematization or parameterization can be used to accurately estimate the total subpopulation count originally present in the sample before the commencement of lysis. This is accomplished by informed back extrapolation of the decay rate (or genesis rate) to a time zero of the analysis process. This zero time is defined and known as the instant when erythrolytic agents were added to—or adjustments were made to the physico-chemical condition of—the sample solution in order to initiate erythrolysis. On the other hand, this parameterization leads to novel information useful both in cell classification and in the diagnosis of disease.

It is not the recognition of the general biological principle that cell subpopulations or clones behave homogeneously which represents the invention, but rather its exploitation in the context of the saltatory temporal differential survivorship lysis during the everyday laboratory task of reliable cell counting.

According to the present method, a cell lysis or decay rate is attributed to—and calculated for—entire populations of cells (the entire iceberg), rather than for the individual cells (iceberg tips or snowflakes) contained within a pure or heterogeneous suspension of cells. This is possible because of the high degree of structural similarity among cells within the same homogeneous clonal population. From countless studies we conclude that this structural similarity is reflected in the experimentally determined functional similarity of the saltatory lytic response amongst the members of such populations. Samples analyzed according to the method of the present invention which contain a population of cells exhibiting a few fragile cells —e.g. a population of lymphocytes from chronic lymphocytic leukemia—show that the entire cell population has an altered behavior pattern, not just the few fragile members noticed in a "bad" blood film. We have learned that every member of every subpopulation in a blood sample has been affected rather similarly during in vitro blood storage which results in bad blood films—but there are differences in the rates at which the differing blood cell subpopulations within a stored blood sample suffer. We have learned that every member of the clonal cell population which exhibits a few "stress induced" fragile cells in blood films on fresh blood samples is more sensitive to lysis than corresponding cells in unaffected leukocyte populations (such as basophils or eosiniphils) which do not exhibit fragile cells under the shear stress of blood film preparation. Of course, there are also clonal abnormalities at an earlier stage of leukocyte differentiation. Mutations at the stem cell level of all blood cells can therefore affect the lysis characteristics of several blood cell populations simultaneously—just as poor anticoagulation methods and adverse blood storage conditions will affect many subpopulations simultaneously.

The present method is advantageously applied to many different cell systems and many different cell detection systems. It can be practiced with most of the known cell categorization techniques in which cells are diluted. This method can also be applied prospectively to newly developed cell categorization techniques because of its reliance upon measurement and use of a homogeneous, specific, clonal cell decay or genesis rates. The operation of generating these rates is independent of cell type and of cell counting technique. The present invention can be practiced on automated cell counting instruments such as those which utilize electrical impedance as a measurement of cell size to identify, characterize, categorize and enumerate cell populations (e.g. Coulter S Plus IV Blood Cell Analyzer and the impedance and optic transducer modules of the CELL-DYN ® 1600 Blood Cell Analyzers).

For example, the present invention can be implemented on instruments which employ optical flow cytometry, such as selective fluorescence staining or tagging and light scatter or absorption phenomena to categorize and enumerate cell populations (Cytometry, 3; 68–74, 1992; Becton-Dickinson FACScan and FACSort systems and Abbott CELL-DYN ® 3000 and 4000 series of instruments). This listing of instrumentation is intended to be illustrative, not limiting, of the techniques which can be employed for cell identification, characterization, categorization and enumeration according to the method of the present invention. Optical, electrical resistivity, electrical capacitance, ultrasonic and many additional cell sensing principles can all be combined in a simultaneous or sequential fashion to interrogate each element of a fluid for the presence or absence (or appearance or disappearance) of the signal producing cellular or cell-like structures. These structures can be intact cells, condensing cells, dead cells in various stages of degradation, cell components released after initiation of the lysing process, nucleated cell carcasses, anucleated cell remains or classical cell ghosts and, particularly for plants, cell vacuoles. They can be any particulate, interfering structures or structures of interest which become visible or have become invisible in other windows of observation.

These described counting systems merely serve as a convenient means for illustrating principles of the present invention. According to one method, a sample solution comprised of at least two populations is presented to a counting instrument. A reagent is then added to induce complete cytolysis of one (second) cell population and to enable cell identification, categorization and enumeration of cells in another (first) cell population. In the determination of the decay pattern of the first cell population, it is usually convenient to designate as time zero of the cell processing cycle the time at which the lyse-inducing reagent is added to the sample solution. In certain known counting instruments, the diluted, lysed sample solution is made to flow through a detector region, essentially cell by cell, for measurement of signals related to cell type and number of cells in the first cell population.

However, the addition of a lyse-inducing reagent to the sample solution at the beginning of the sequence is not instantaneously followed by the commencement of flow of the diluted, lysed sample through the signal detector region. Ideally, there should be completed lysis of the second cell population but there may also be some inadvertent, commenced decay in the first cell population by the time that the diluted, lysed sample solution begins flowing through the detector region. Traditionally, it is the numerical cell concentration of the first cell population (leukocytes) which we wish to know accurately. To this end, the behavior of each visible cell population over time is observed and calculated. The intact cells and potentially visible carcasses of the second population may provide heuristic information beyond that necessary to ensure accuracy of the estimated numerical concentration of the first cell population.

Figure 9:
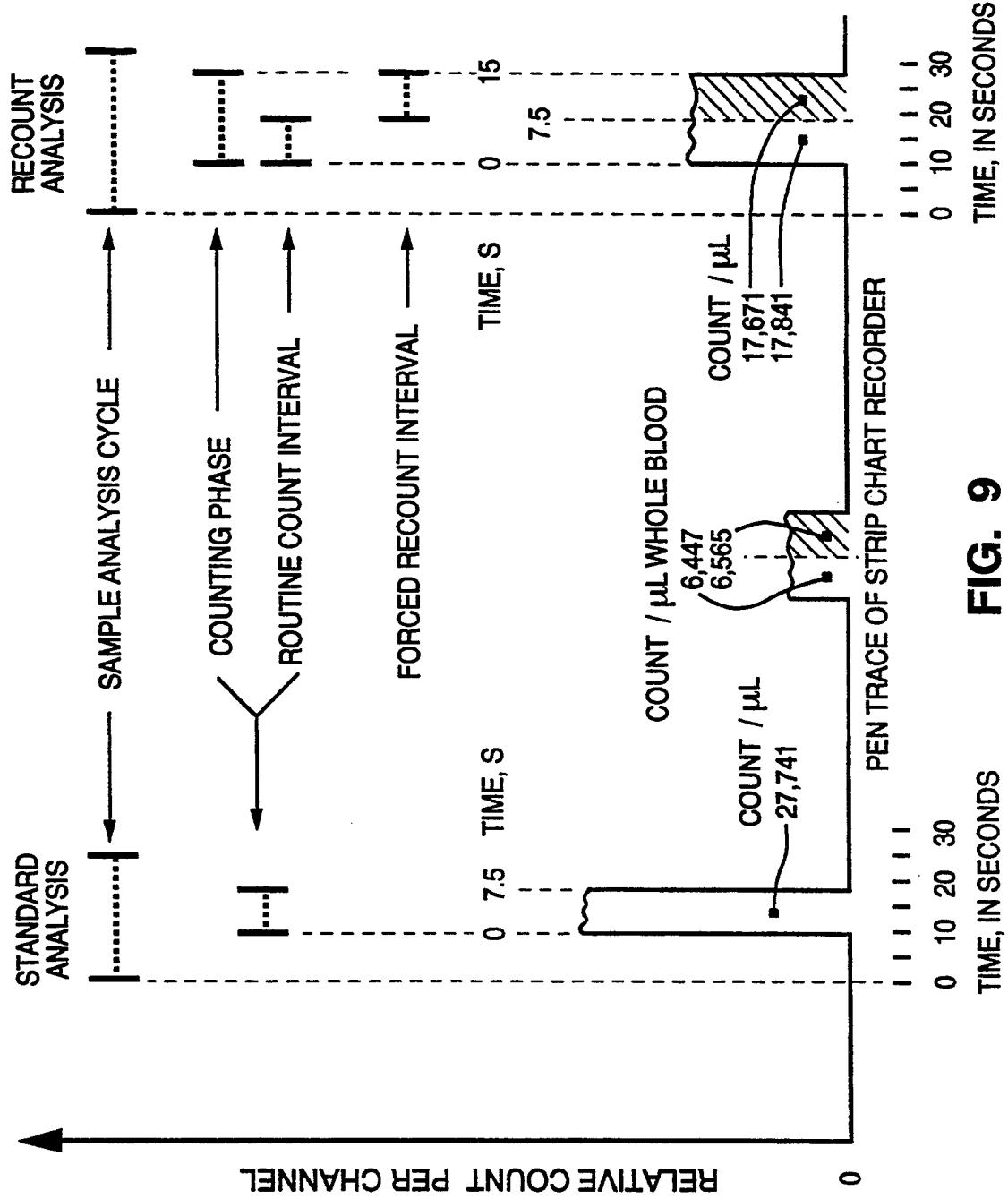
FIG. 9 is an analog plot of observed CELL-DYN® 3000.1 leukocyte cell counts versus time for whole blood samples from subjects without lyse-resistant erythrocytes and without lyse-sensitive leukocytes. The tracings of the strip chart recorder demonstrate count rate monitoring according to a method of the present invention. The figure shows one cell analysis cycle using only the routine counting phases and two cell analysis cycles employing forced recounting.
Figure 10:
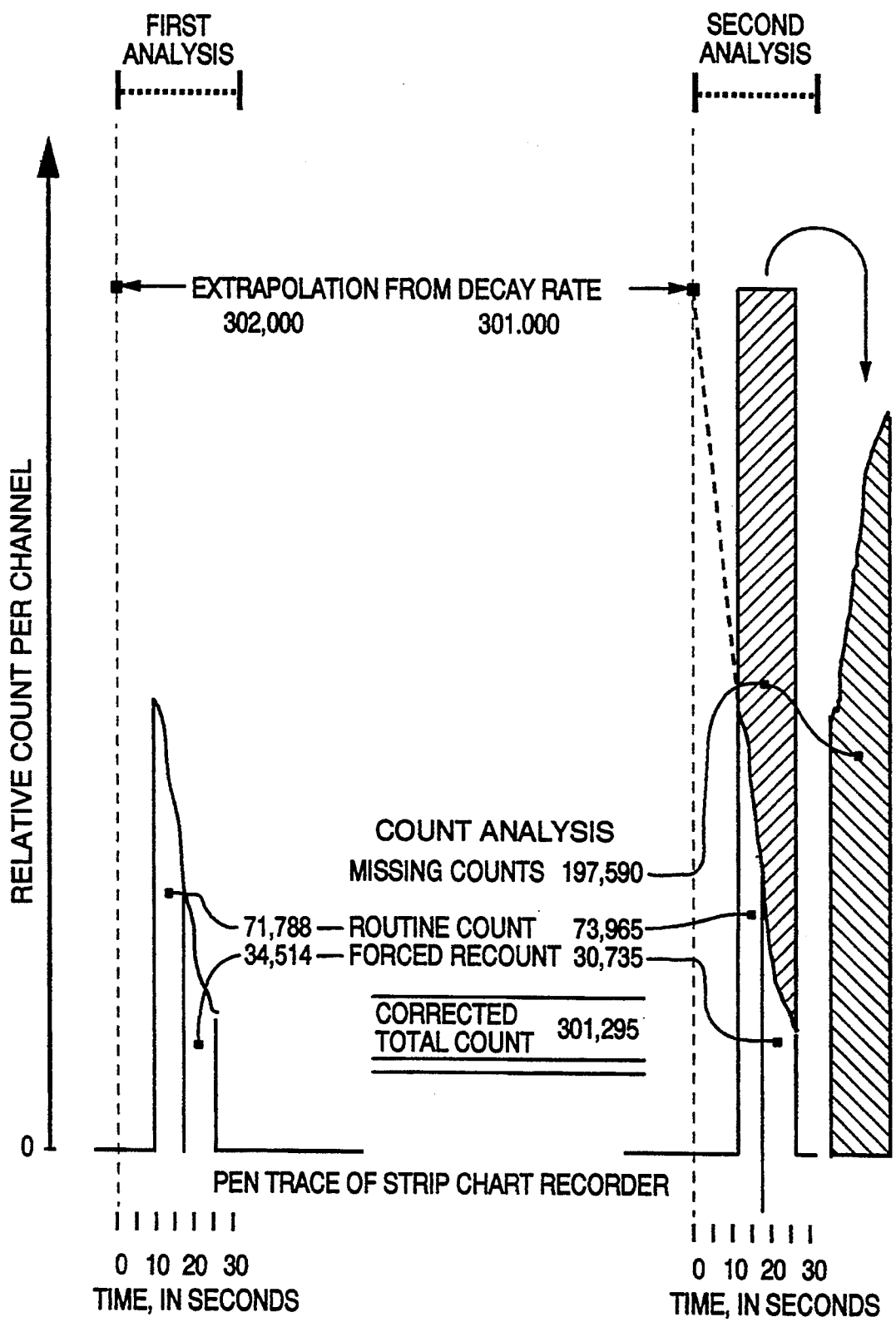
FIG. 10 shows two analog plots of observed CELL-DYN® 3000.1 leukocyte cell counts versus time for a single whole blood sample from a subject with chronic lymphocytic leukemia. The second analysis has been resolved into one-third of recovered or visible cells and two-thirds of lost or invisible cells.
Figure 11:
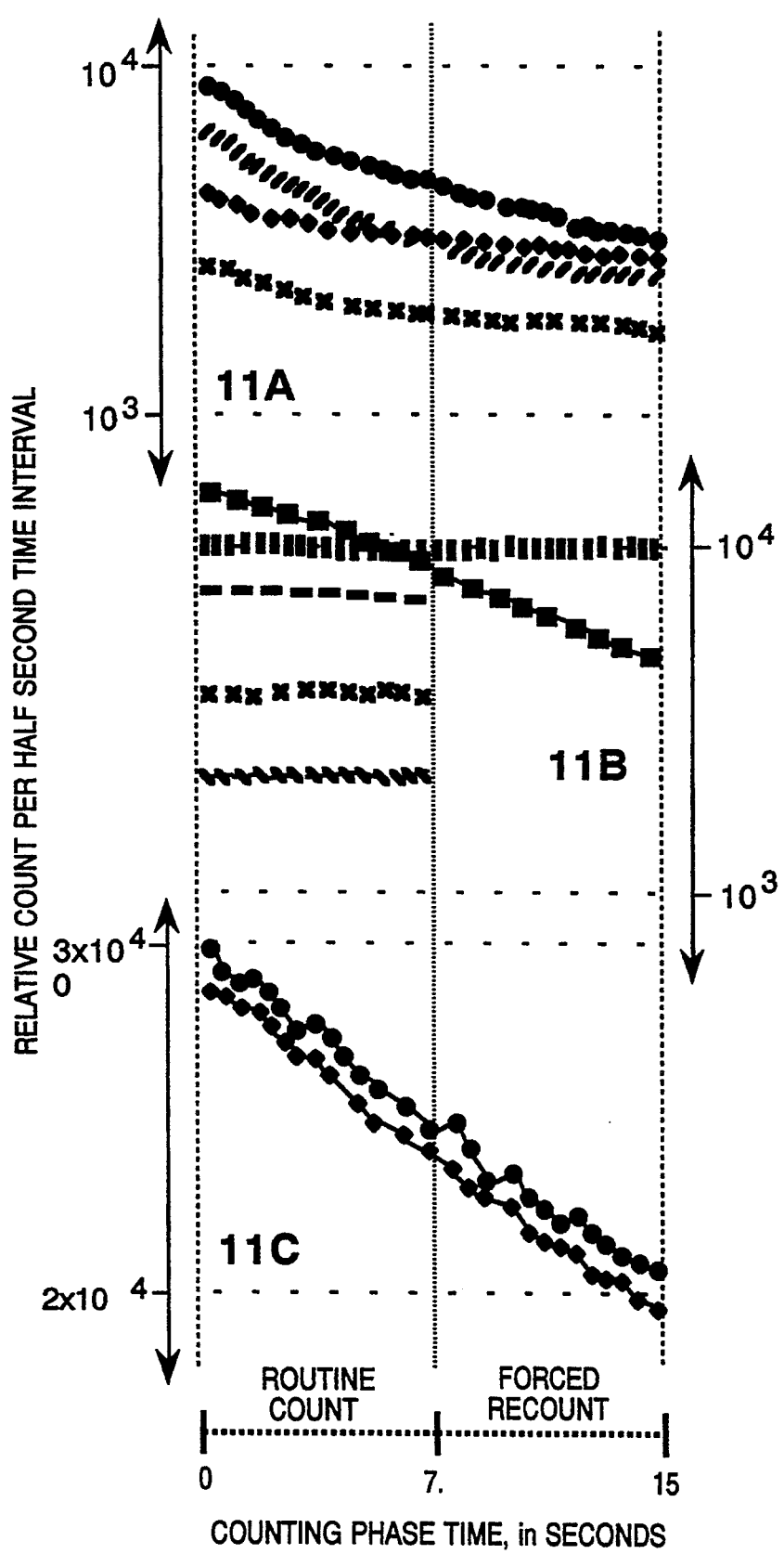
FIG. 11 shows a digital plot of the log of counts versus time for the count phases of sample processing cycles performed on a CELL-DYN® 3000.2.

After constant volumetric flow conditions are established in a blood cell counter or analyzer signal detectors capture the signal generated by visible cell structures. These signals may include an elapsed processing time signal which uniquely identifies each cellular structure (or sequential groups of cells) passing through the detector region(s). This signal generation and detection phase continues over a period of time after commencement of the count acquisition phase. During this phase of continuous steady flow of diluted sample through the detector region, count data per unit volume of sample is collected on all cellular structures which are within view during two or more time intervals of the counting phase. During a particular time interval, the automated instrument will use all generated signals to store and provide count information on all visible cellular structures flowing through the detector region. These may belong to either the first or second cell population present in a discrete volume of the diluted sample. During part A of the counting phase of the sample analysis cycle (FIGS. 9 and 10), the raw count data for each cell population is then used to generate a cell count per unit volume per unit mean time A. Next, the instrument generates a cell count per unit volume based upon the analysis of a second discrete volume of the diluted sample passing through the detector region at the later mean time B during the counting phase (FIGS. 9 and 10). This counting procedure may be repeated over short time intervals throughout the counting phase as the sample solution passes through the detector region (FIG. 11). Adjustments are made to the raw data for sample dilution and for any other reagent addition(s).

The cell counts generated at mean times A and B (and, optionally, at subsequent times) are then used to calculate a cell decay rate by fitting a curve through the observed data points and extending the curve back to time zero of the cell analysis cycle (FIG. 10). Certainly more data points than counts at mean times A and B may be used in the generation of a cell decay rate. Two points and a single decaying cell population merely represent the minimum requirement for any useful curve fitting technique. The rate function is back extrapolated to time zero of the sample analysis cycle in order to provide an accurate count rate for the cell population initially present in the sample solution. This back extrapolation corrects cell counts which would be inaccurate after reagent addition whenever the decay rate is significant (either positive or negative) due to inadvertent lysis of the desired cells or to incomplete lysis of interfering cells. This correction may utilize a significant (non-zero) negative decay rate for the intact cells or it may utilize a significant (non-zero) positive genesis rate for the appearance of cell structures such as degenerated cells, cell ghosts or residua. The concept of decay rate for the initial cells of interest is intended to cover both of these transition rates—appearance and disappearance.

We have shown that present state of the art flow cytometric instruments using various cell sensing principles—including light scatter data—as indicative of cell type and number of cells can be modified to add a time element to the listing of the data for each cell which passes through the detector region. This "time tag" is then used to calculate a cell decay rate which enables computation of the number of cells present in an unstable population at time zero of the cell processing cycle.

However, such digital data processing is not essential to practice the present invention. As shown in FIGS. 9 and 10, under suitable cytolytic modes of operating standard flow cytometers, two consecutive counts on a suitably prepared sample will give the minimum necessary information to practice this invention. In the past the "unstable" counting conditions illustrated by the first analysis of FIG. 10 had to be avoided at all cost—though this was frequently impossible. Now such very stable instabilities can be exploited systematically as illustrated with the second analysis of FIG. 10.

A preferred embodiment of the present invention is described herein with reference to the identification, characterization, categorization and enumeration of leukocyte cell populations present in whole blood samples. This cell system has been extensively studied and the present invention provides important enhancements to existing blood cell counting systems. These enhancements extend the capability of these systems by improving the accuracy of the count data. The invention further enables the identification of certain abnormal cell types or conditions based upon the exploitation of cell decay and/or the rate of cell decay.

In order to count the leukocyte population in the presence of erythrocytes without resorting to very expensive technology, it is first necessary to lyse the numerous erythrocytes which dominate FIG. 1. This is done to enable visualization of the less numerous leukocyte populations utilizing relatively simple and cost effective detection principles. There are, however, conditions which tend to make erythrocytes more lyse-resistant. As already stated above, erythrocytes are more difficult to lyse in blood samples from the human fetus, from neonates, from certain non-human mammalian species, from patients with hemoglobin disorders and from patients with increased concentrations of plasma proteins. Lyse-resistance of erythrocytes creates a dilemma in that inadequate erythrolysis tends to result in poor leukocyte count information because unlysed erythrocytes tend to swamp the sensors. On the other hand, the use of a stronger erythrolytic agent to insure thorough erythrolysis also has a negative effect upon the accuracy of the leukocyte counts because of inadvertent leukolysis.

According to one embodiment of the present method, a strong erythrolytic agent is used to ensure complete erythrolysis, even in the cited situations in which these hard-to-lyse erythrocytes have heretofore proven extremely troublesome. Any adverse effect on the leukocyte population resulting from the strongly erythrolytic conditions is corrected by the use of a calculated leukocyte decay rate or pattern. This is back extrapolated on an individual leukocyte population basis to accurately estimate the leukocyte count rate at time zero of the cell analysis cycle (FIG. 10).

According to another embodiment, the method of the present invention is used to detect the presence of—and to correctly enumerate—so-called fragile lymphocytes present in a whole blood sample. It is known that lymphocytes are lyse-sensitive in patients suffering from chronic lymphocytic leukemia, from infectious mononucleosis, and from a few other disorders. This lyse-sensitivity implies that a significant number of lymphocytes will lyse under the conditions necessary to exceed the cytolytic threshold for erythrocytes. This occurs even when elaborate and expensive cell distorting and cell fixing and stabilizing systems are used in a vain attempt to fully counteract this clonal lyse-sensitivity.

In the practice of this embodiment, the strong erythrolytic agent which overcomes lyse-resistant erythrocytes is still used but the lymphocyte count is monitored closely over time. Lymphocyte counts are taken at selected time intervals after the addition of the erythrolytic agent while the sample flows through the detector region. These lymphocyte counts are then analyzed as a function of time to determine whether there is a measurable degradation in the number of lymphocytes present in the sample solution. At least one threshold value for the decay rate is then established as indicative of the presence of lyse-sensitive lymphocytes. This information can be used to intercept and thereby to assist in diagnosing the clinical condition of the patient from whom the sample was drawn. Such screening information can be extremely valuable. The information can also be used to monitor the effectiveness of the therapy used to treat the disorder. It can even be used to discriminate between newly enabled subcategories of known disorders.

Optionally, in this embodiment, the lymphocyte count information from the different time intervals is used to generate a lymphocyte decay rate by linear curve fitting techniques. This enables estimation of the correct lymphocyte count by back-extrapolation of the count rate pattern to time zero via the decay rate information. Accurate estimation of the total lymphocyte population initially present in the sample solution is then possible.

Complete erythrolysis can also be obtained by mixing filtered sea water and distilled water in a ratio exceeding four volumes of the extremely hypotonic distilled water to every one volume of the approximately isotonic sea water. The resulting strongly erythrolytic and very hypotonic diluent would be advantageous for reliably counting the leukocyte population because of the low cost and world wide availability of the reagent. However, this ideal erythrolytic agent has been quite unacceptable until now because it is also vicariously leukolytic. This leukolytic activity can now be monitored and accounted for in the final total and subtotal leukocyte count.

CELL-DYN ® 3000 SERIES OF INSTRUMENTS

In a preferred embodiment of the present invention, the Abbott CELL-DYN ® 3000 performs a conventional five leukocyte subpopulation differential with flagging recognition of the additional cell types which do not normally circulate (NCCLS H20-A). Prior to the addition of the presently disclosed fifth temporal dimension, the leukocyte differential data of the CELL-DYN ® 3000 was based only upon four dimensional light scattering characteristics of unstained leukocytes. This prior approach is described in our copending U.S. patent application Ser. No. 07/352,106, filed May 15, 1989, entitled FLOW CYTOMETRY LYTIC AGENT AND METHOD ENABLING 5-PART LEUKOCYTE DIFFERENTIAL COUNT, now abandoned. The relevant portions of this patent application are incorporated herein by this reference.

In the CELL-DYN ® 3000, sample processing begins with aspiration of 150–350 μL of whole blood (depending on sampling mode). Aspiration may be accomplished via an open or closed tube sampler and either with manual or automatic sample presentation depending upon the type of instrument used. The aspirated sample passes into a shear valve which isolates three precise aliquots. A 32 μL aliquot of the blood is diluted 250 times with erythrolytic agent and transported to the optical transducer for determination of the total leukocyte count (WBC) and the leukocyte differential. A 12 μL aliquot of the blood is diluted 250 times with hemoglobin reagent and transported to the hemoglobin transducer, a spectrophotometer known as the hemoglobinometer. A 0.8 μL aliquot of the blood is diluted 12,500 times with approximately normotonic blood diluent and transported to the impedance transducer for generation of the thrombocyte and erythrocyte pulse data.

WBC AND LEUKOCYTE ANALYSIS

Figure 7:
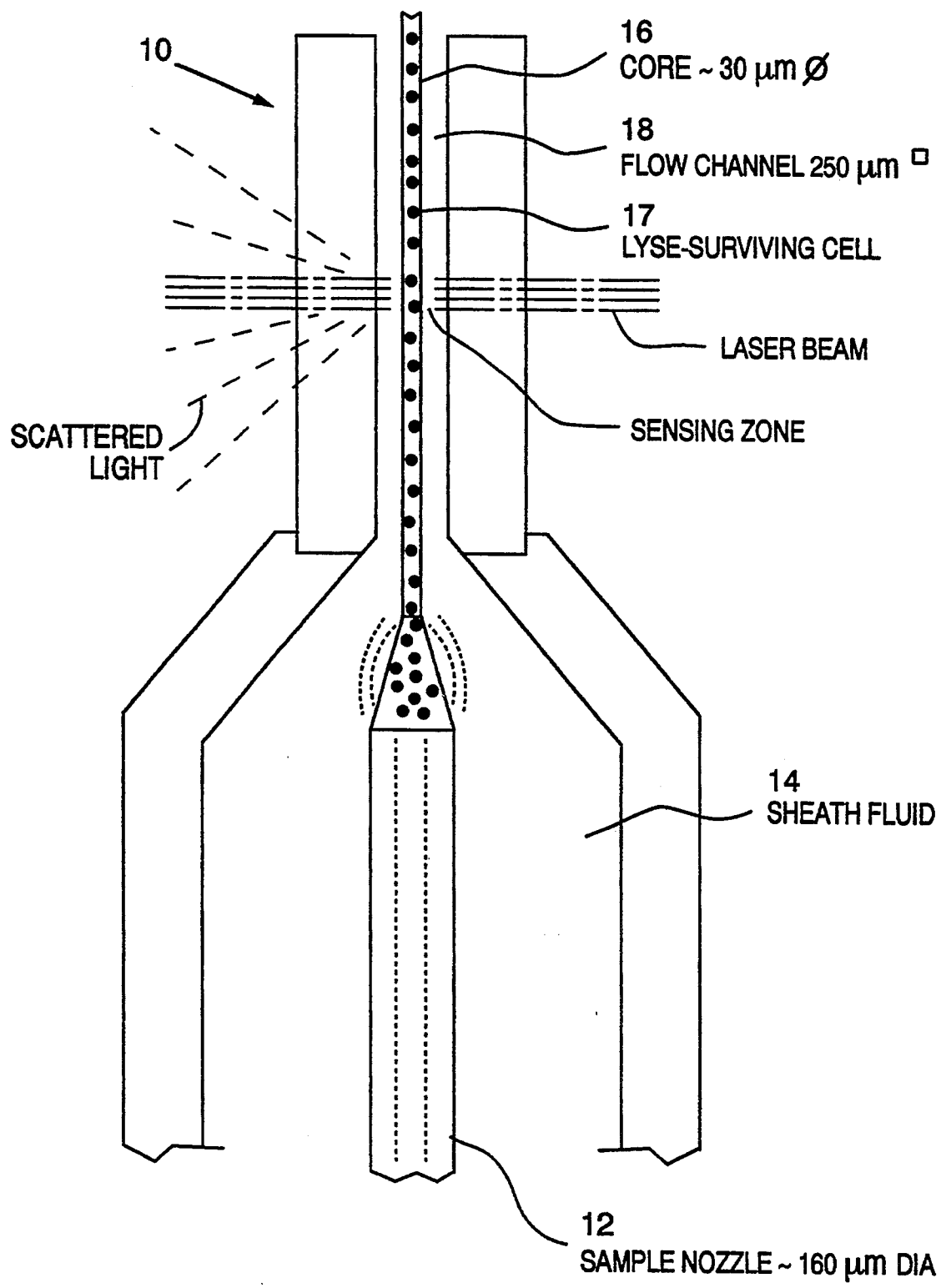
FIG. 7 is a cross sectional, schematic view of the sensing zone and flow cell regions of the optical transducer of the CELL-DYN® 3000 instruments.

The CELL-DYN ® 3000 uses an optical transducer to measure the light scattering characteristics of leukocytes. The flow cell 10 of the transducer are shown diagrammatically in FIG. 7. A suspension of blood in which the erythrocytes have been nominally lysed is propelled at low velocity from the sample nozzle 12 where it comes into contact with a fast moving, laminar flow, sheath stream 14. In a process known as hydrodynamic focussing, the sample stream is attenuated to a central core 16. In the fused silica flow cell this core is 25–30 μm in diameter. This arrangement usually ensures that only a single leukocyte is in the sensing region of the laser beam # at any given time. Therefore coincidence problems are minimized. If erythrocytes had not already been efficiently lysed, there would typically be over one hundred interfering erythrocytes present in this sensing zone. Furthermore, since the physical aperture is large (250 μm square) the flow channel 18 is unlikely to clog. Yet it is still able to give the resolution of the much smaller apertures used in impedance transducers.

Figures 8, 8A:
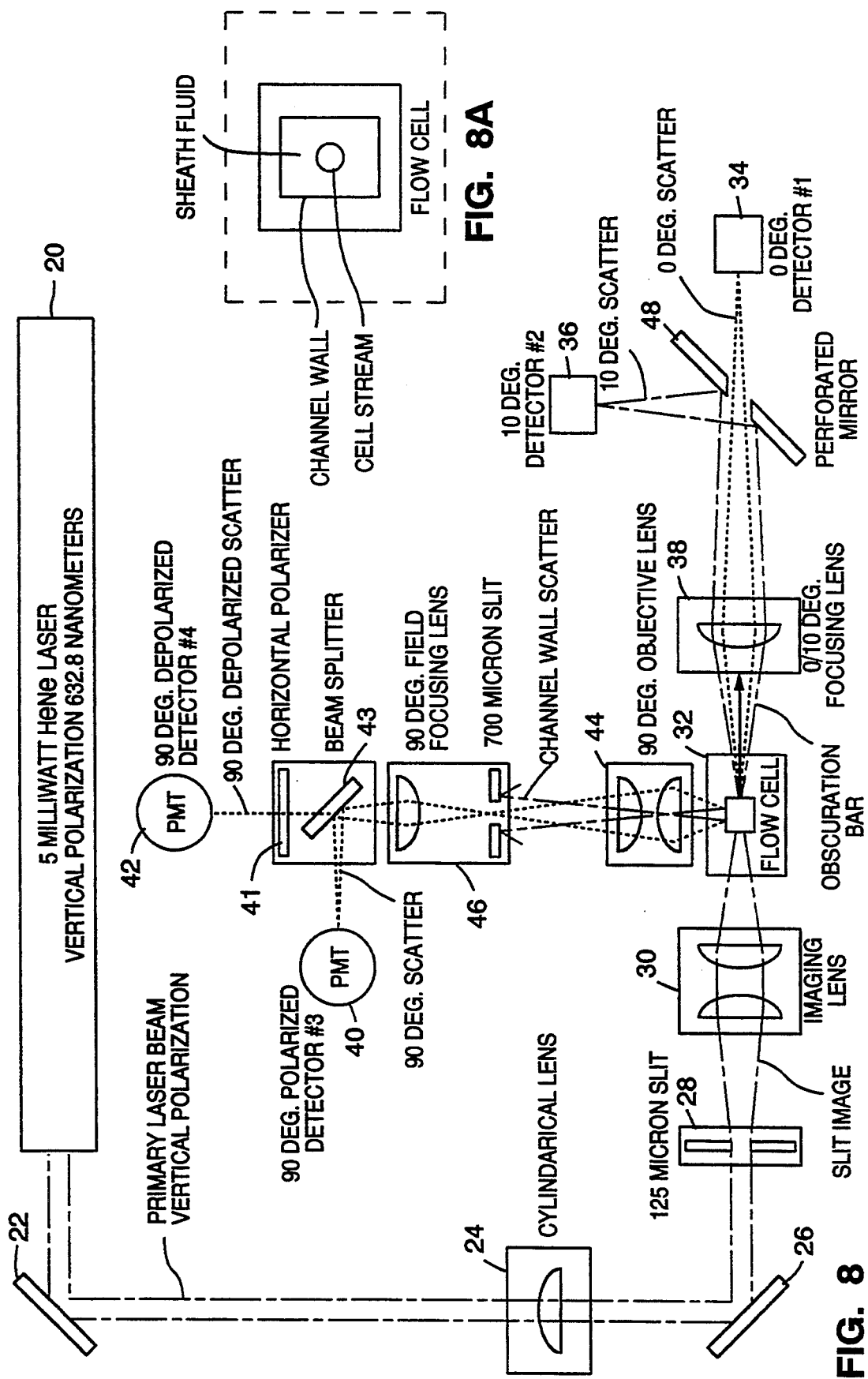
FIG. 8 is a diagrammatic representation of the optical bench of the CELL-DYN® 3000 instrument line.

FIG. 8 shows a diagram of the CELL-DYN ® 3000 optical bench. The specification of our U.S. Pat. No. 5,017,497, entitled PARTICLE DISCRIMINATOR AND METHOD, is herein incorporated by reference. The light source 20 is a polarized 5 mW helium-neon laser with a wavelength of 632.8 nm. The laser head is oriented so that the plane of polarization is vertical. The laser beam is shaped and focussed by a front surface mirror 22, a cylindrical lens 24, another front surface mirror 26, a vertical slit 28, and a lens 30. This shaping ensures that the beam intensity in the region of the central core 32 of the sample stream is Gaussian with a 'one over e squared' diameter of about 70 μm. In the horizontal plane the energy profile shows a 'top hat' appearance with a flattened top about 80 μm wide. This arrangement ensures that the instrument will continue to give reliable data even if the sample core wanders slightly from its normal position.

A lyse-surviving leukocyte that enters the focussed laser beam will scatter light in all directions. Since the wavelength of the light is small compared with the cell size, this scattering phenomenon is described by Mie theory and by a Miller matrix. A part of the scattered light is collected by four photodetectors. Two silicon photodiodes 34 and 36 measure light scattered at half angles of about 1-3 degrees and about 3-10 degrees with respect to the axis of the laser beam. These photodiodes 34 and 36 are respectively termed the '0 degree' and '10 degree' detectors. Direct laser light is blocked by the obscuration bar 38. Light scatter at these low angles is a complex function dominated by cell size with some contribution from cell structure or complexity.

Light scattered at 90 degrees to the axis of the laser beam is collected using two photomultipliers (PMTs) 40 and 42. Photomultipliers, not photodiodes, are used in the 90 degree channels because relatively little light is scattered at high angles. If the impinging polarized light is merely reflected from a single surface, it retains its original vertical plane of polarization. However, if it is reflected many times within a cell—as by many granules or anisotropic structures—then the scattered light can have an altered angle of polarization. In order to exploit this phenomenon in the CELL-DYN® 3000, one of the PMTs 42 has a horizontal polarizer 41 in front of it. This polarizer prevents vertically polarized light from striking the photomultiplier. Therefore, any light detected by the '90 degree depolarized' PMT 42 is light that has been 'depolarized' by its interaction with a cellular structure—usually a leukocyte. The second photomultiplier 40 (termed the '90 degree total' PMT) receives the scattered light reflected off a cover glass 43 that is angled at 45 degrees. The major portion of this orthogonal light is still vertically polarized. Hence, this sensor, 40, is a good monitor of the total light scattered in the orthogonal direction.

An objective lens 44 and a scatter stop 46 complete the orthogonal scatter channels. The low angle scatter channels also include a perforated mirror 48.

Data obtained from the four photosensors is used to construct a four dimensional scattergram (FIG. 6). This can be viewed using the computer graphics capabilities of the instrument which enable a three-dimensional "solid" representation to be rotated in space—with the fourth dimension made manifest through selection of different colors for the pixels representing differing pulse magnitudes in that fourth dimension. For purposes of paper documentation, the four-dimensional scattergram can be examined by six user selectable pairs of two dimensional scatter plots or projections—and by numerous user selectable one-dimensional histogram projections. Two two-dimensional representations of the four-dimensional scattergram are shown in duplicate in FIGS. 6A and 6B. The one-dimensional histograms are analogous to the format shown in FIGS. 4 and 5.

The lytic agent used for the leukocyte count and for differentiation of the leukocytes into the subpopulations (or WBC) is best formulated to rapidly and completely lyse erythrocytes. The CELL-DYN ® 3000 may utilize a lysing agent which consists of an aqueous solution of an aromatic oxyethanol, an organic buffer (having pH at or near 8.5, which serves to provide pH buffering capacity and to increase electrical conductivity of the lytic agent) and a non-ionic detergent component. The aromatic oxyethanol used is preferably 2-phenoxyethanol. The organic buffer is selected from the group consisting of TRIS/HCl, boric acid, glycylglycine and BICENE. The non-ionic detergent is selected from the group consisting of Triton X-100, Triton X-114, and polyoxyethylene or saccharide-derived detergents. Before introduction of the present invention, the preferred lytic agent consisted essentially of 2-phenoxyethanol at a concentration between 20 mM and 80 mM, TRIS/HCl buffer and Triton X-100.

In a particularly preferred embodiment for exploitation of the present invention, the lytic agent comprises an aqueous solution of Triton X-100, 2-phenoxyethanol, and TRIS/HCl buffer. Whole blood is mixed with an excess (typically fifty-fold) of this lytic reagent. Saltatory kinetic lysis of the red blood cells occurs extremely rapidly due to the combination of osmotic shock, the action of the non-ionic detergent and the pH of about 8.5. The optimal formulation of the lytic agent is given below:

2-phenoxyethanol (a liquid at 25° C.) . . . 750 mL
TRIS/HCl buffer, pH 8.5 (500 mM TRIS)
titrated to pH 8.5 with 1 M HCl . . . 1500 mL
0.5% (vol/vol) aqueous Triton X-100 . . . 100 mL
Deionized water to . . . 100 L In the optimized formulation, 2-phenoxyethanol is present at a concentration of about 41 mM, although a useful range of concentrations exists between 20 and 80 mM. The pH of the TRIS buffer may be decreased to pH 8.1 without significant effects on its performance. If the pH of the buffer is increased above 9.0, the reagent becomes more erythrolytic and more rapid saltatory kinetic leukolysis will occur. The presence of trace amounts (up to about 5% vol./vol. of Triton X-100) or a similar non-ionic detergent helps to ensure complete erythrolysis in specimens which are typically regarded as difficult to lyse, but this also accelerates saltatory kinetic leukolysis. Prior to the present invention this was a dilemma for blood samples with fragile leukocytes and in blood samples with lyse-sensitive cells because of in vitro storage of the blood beyond four to six hours.

Other organic buffers may be substituted for TRIS/HCl. Among those with pH at or near 8.5 are boric acid, glycylglycine and BICINE (available through CalBiochem) which may be used in the lytic agent. Triton X-114 can be used as the non-ionic detergent component of the lytic agent. Other hydrophilic detergents may be selected from those having polyoxyethylene or saccharide head groups.

The five-part leukocyte differential is determined solely on the basis of time and light scatter. Since no cytochemical staining is required, the CELL-DYN 3000.2 provides a very cost effective, rapid CBC with WBC diff. Throughput is around one hundred blood samples per hour depending on the manner in which samples are processed. Data produced by the scatter characteristics of each leukocyte is obtained from the four photodetectors which were discussed previously.

FIG. 9 shows count rates recorded with a strip chart recorder coupled to a CELL-DYN ® 3000.1. The data represents three differing whole blood samples in which all erythrocytes have completed their rapid lytic decay by the commencement of the counting phase of the sample analysis cycle. None of the leukocyte subpopulations exhibit a significant inadvertent decay since there is not a substantial decline in the lyse-surviving cell count over time during the typical routine count phase of a sample analysis cycle. To emphasize this stability of the count rate, the analyzer was forced into a recount mode during the sample analysis cycle for sample 2 and 3 of FIG. 9. This recount capability is an extended counting mode normally reserved for automatic occurrence when samples have very low WBC concentrations. No decay is evident over the fifteen seconds of routine and recount times in the leukocyte counts which are shown as relative frequencies on the ordinate and as whole blood counts. The minor irregularity evident in the strip chart count rates is expected on the basis of stochastic randomness of the Poisson type.

FIG. 10 shows the contrasting strip chart results from a subject known to have chronic lymphocytic leukemia. The erythrolytic diluent (as described above) was used for generation of the data shown in FIGS. 9 and 10. It was selected for its ability to sufficiently lyse even the most lyse-resistant erythrocytes. FIG. 10 shows a routine count and a forced recount during each sample analysis cycle. Additionally, two such analysis cycles are performed on the sample. The decreasing leukocyte counts evident from the consistent pattern during reanalysis indicate the presence of at least one lyse-sensitive subpopulation within the heterogeneous or mixed leukocyte populations. The homogeneous fragile lymphocyte population is in the process of being lysed. The dotted curve added to the second trace of FIG. 10 represents the back extrapolation of the leukocyte decay pattern or leukocyte count rate to time zero of the sample analysis cycle. Two back extrapolations yielded initial leukocyte counts of 302,00 and 301,000 cells per micro liter of whole blood. These numbers were confirmed as correct by laborious manual techniques.

By utilizing FIGS. 6, 9 and 10, we can demonstrate how the method of the present invention can be used to specifically identify the presence of fragile lymphocytes in this whole blood sample.

The monitoring of FIGS. 9 and 10 is performed on all the data visible in FIG. 6A. Provided that the instrument is performing correctly, a declining count in this leukocyte region is indicative of the presence of lyse-sensitive cells in the sample. This is because this four-dimensional total leukocyte region has been selected in such a way that, for this diluent, there is no known mechanism by which there could be an increase in the count rate in this total region due to the appearance of cell structures from invisible cells which would need to exist outside the monitored total region. In other words, under the specified analytic conditions, a lymphocyte decay can not be masked by known cell structure genesis or particle genesis.

Next the software algorithm can examine the count rate pattern for this sample by interrogating the four-dimensional pulse sub-region projected as region R in the two-dimensional schematic of FIG. 6B1. [The sample of FIG. 6 does not represent the particular sample of FIG. 10; and it must be understood that the region indications of FIG. 6B are highly dynamic and differ in precise detail from sample to sample.] Region R is where a decaying pulse rate would be expected if hard-to-lyse erythrocytes accounted for the decaying pulse pattern. [Alternately, the dynamically located L/R threshold would move over time in accordance with the present invention.] Region R is also where an increasing count rate can occur when certain anomalous intact leukocytes (for example, from a promyelocytic leukemia) degrade and deliver nuclear remnants into this region. In that case, a count decrease of at least this magnitude would appear in the monitored total region above region R in FIG. 6B.

If such a region-R-specific count increase were accounted for by a reciprocal region M decrease, then we could suggest the interpretation: "An unstable cell region. This is consistent with promonocytic leukemia." In the particular case of FIG. 10, there was neither an increase nor a decrease in the negligibly low but stable count rate in region R. A similar interrogation of, the lymphocyte region, L, accounted for the entire decline in the total leukocyte count region. The conclusion is that a population of fragile or lyse-sensitive lymphocytes has been discovered and that viral infections and leukemias must be considered. In view of the very high corrected lymphocyte count of 299,000 per microliter whole blood, the interpretive report of the instrument may supplement the correct numerical output with: "The lymphocyte population is very fragile with a standardized decay rate of + + + + under the present analytic conditions (Normal value: 0). The reported count of 299,000 lymphocytes per $\mu$l whole blood has been corrected for this in vitro decay phenomenon. This blood picture is consistent with a diagnosis of chronic lymphocytic leukemia."

According to this preferred leukocyte embodiment of the present invention using the CELL-DYN ® 3000.2, all erythrolyse-surviving cell structures are count rate monitored during the counting phase of a sample processing cycle. A surviving cell count for each five hundred millisecond interval is obtained by the light scatter technique.

FIG. 11 illustrates the type of decay rate data generated by the CELL-DYN ® 3000.2 in this manner. FIG. 11A represents total leukocyte count rates obtained on four neonatal blood samples with so-called hard-to-lyse erythrocytes. The entire count decline was accounted for by decay in regions R and L of FIG. 6. The interception of this problem now permits the CELL-DYN ® 3000.3 to wait forty-five seconds after the initiation of the sample analysis cycle of FIGS. 9 and 10 and to commence the counting phase thereafter. Under these analytical conditions the erythrocytes of neonates no longer encroach on region L of FIG. 6; and all the leukocyte subpopulations generally still give stable count rates and correct counts on such fresh blood samples.

FIGS. 11B shows decay patterns observed on blood samples from five different subjects with chronic lymphocytic leukemia in various stages of therapy. One of these patients had a standardized lymphocyte fragility of + + + + which is comparable to that seen in FIG. 10. The middle two had a fragility of + + and the remaining two had a fragility of +. The fact that the fragility was not statistically negligible is illustrated by analogy with FIG. 11C. In that figure the ordinate graduation is arranged to reveal much higher resolution. In FIGS. 11A and 11B the counts increase by a factor of ten from the lower to the higher horizontal ordinate guidelines. In FIG. 11C the increase is only a factor of 1.5. If the two plots of FIG. 11C were represented on the lower resolution grids, they would actually also appear to be almost horizontal lines—like four of the CLL plots in FIG. 11B.

The patients shown in FIG. 11C have hard-to-lyse erythrocytes—like those in FIG. 11A. However, the subjects are adults and the mechanism is a hemoglobinopathy—rather than a combination of the physiologically different hemoglobin A of neonates together with a coupled difference in shape of those cells. In the case of FIG. 11C the decay was accounted for entirely by a decay rate in the region R of FIG. 6B1. Consequently, the WBC would not have been erroneous for these samples in the CELL-DYN® 3000.1. On the other hand, the invention incorporated into the CELL-DYN® 3000.2 (and 3000.2 A) permitted the successful totally unanticipated interception of a congenital abnormality in the hemoglobin of these two patients. This cost-effective annotation of the hematology report is clinically very useful in many circumstances. It represents the incorporation into erythrolytic leukocyte analyses of the experimental approaches described in the context of FIGS. 2 and 5. This novel and powerful erythrocyte fragility approach has significant potential for extensive further optimization through appropriate selection of the erythrolytic reagents.

The CELL-DYN® 3000.1 or 0.2 processes the leukocytes in a single pass through the flow cell. A modified version of the CELL-DYN® 3000 called the CELL-DYN® 3000A is also capable of utilizing the method of the present invention. The CELL-DYN® 3000A employs two channels for processing leukocytes. It utilizes the optical channel of the CELL-DYN® 3000 and the impedance channel of the CELL-DYN® 1300. The impedance channel employs the familiar technique of measuring changes in electrical resistance produced by a particle as it passes through a small aperture. A similar technique is described in our U.S. Pat. Nos. 4,710,021, 4,745,071 and 5,045,474.

In the CELL-DYN® 3000A, the impedance channel processes lysed whole blood to obtain the total leukocyte count by enumerating leukocyte nuclei from intact cells from which cytoplasm has been "stripped normotonically" in a gentle but specific manner. This allows the back-extrapolated leukocyte count from the optical channel to be confirmed by the totally independent differently optimized leukocyte count from the impedance channel. Confirmation is possible because the nuclei counted in the normotonic to slightly hypertonic impedance channel are not sensitive to progressive leukolysis. A dual channel approach in a CELL-DYN® 3000.2 A enables the operator to confirm the presence of fragile leukocyte populations as there will be an observable disparity between the raw count rates from the optical channel and those from the impedance channel.

It should be emphasized that, at this stage of exploitation of the present invention, there will not be any significant discrepancy between the decay corrected optical WBC—termed WOC—and the refined and, if necessary, also decay corrected nuclear impedance WBC—termed WIC. However, availability of data by both methods will aid in the establishment of the new efficient corrected WOC even in extremely simple instruments capable of running the entire blood analysis utilizing only filtered and partly diluted sea water. The possibility of modulating the erythrolytic approach separately in the WOC and WIC channels of the CELL-DYN® 3000A also permits establishment of the newly enabled "relative lyse sensitivity" decay rate parameters.

HEMOGLOBIN TRANSDUCER

The CELL-DYN® 3000 and 3000A instruments measure hemoglobin as a heme-cyanide complex associated with quaternary ammonium salts.

A 12 $\mu$L aliquot of blood is diluted 250 times with erythrolytic hemoglobin reagent and transported to the hemoglobin spectrophotometer. The hemoglobin reagent is a mixture of a quaternary ammonium salt/KCN solution with a diluent. The diluent has pH of 7.4±0.05 and an osmolality of 340±3 mOsm. It has the following composition: NaCl, 7.9 g/L; KCl, 0.4 g/L; NaH$_2$PO$_4$, 0.2 g/L; Na$_2$HPO$_4$, 1.9 g/L; Na$_2$EDTA, 0.3 g/L; NaF, 0.4 g/L; 2-phenoxyethanol 3 ml/L and water to make 1 liter. In the best version for the hemoglobin analysis, the quaternary ammonium salt solution consists of tetradecyltrimethylammonium bromide 90 g/L and potassium cyanide 0.75 g/L, mixed into a liter of deionized water. Two liters of this quaternary ammonium salt solution are mixed with 10 liters of the diluent. Finally, Triton X-114 is added at a concentration of 0.25 mL/L.

In this reagent the erythrocytes rapidly release their hemoglobin which reacts with the cyanide and quaternary ammonium to form a stable complex. This complex is passed through the hemoglobin transducer and is measured by determination of absorbance at 540 nm in a 1 cm path length flow cell. This measurement is evaluated against a similar measurement on a reagent blank. The hemoglobin result is reported in terms of its concentration in whole blood. The user may select any of the following units: g/dL, g/L, or mmol/L.

THROMBOCYTE AND ERYTHROCYTE POPULATION PARAMETERS

An 0.8 $\mu$L aliquot of blood is diluted 12,500 times with the diluent described under hemoglobinometry and transported to the impedance transducer for generation of the thrombocyte and erythrocyte pulses.

Each pulse generated by a particle passing though the impedance sensing zone is amplified and compared to internal reference voltages. Thrombocytes and erythrocytes are thereby discriminated in the erythrocyte/thrombocyte channel. The number of pulses is indicative of the cell count, and the amplitude of the pulse is related to the cell volume. Frequency distributions of the pulse amplitudes create the volume histograms shown in FIGS. 4A and 4B.

The histogram of FIG. 4A is used to derive the following thrombocyte parameters: PLT (platelet count), MPV (Mean Platelet Volume), PDW ("Platelet Distribution Width" or rather ten times the geometric standard deviation for the log normal distribution) and PCT (plateletcrit or thrombocrit) as well as various alerts for the thrombocyte population.

The histogram of FIG. 4B is used to derive the following erythrocyte parameters: RBC (Red Blood cell Count), MCV (Mean Corpusal Volume), RDW (Red Cell Distribution Width or rather the coefficient of variation of the distribution) and HCT (Hematocrit), as well as various interpretive analyses for the erythrocyte population. Additionally, the following parameters are computed in conjunction with the hemoglobin value, HGB: MCH (Mean Corpuscular Hemoglobin content) and MCHC (Mean Corpuscular Hemoglobin Concentration) as well as various interpretive analyses.

The volume of diluted blood passing through the transducer during data acquisition must be known in order to obtain absolute cell counts. For the thrombocyte/erythrocyte channel, this is achieved using a metering tube as described in U.S. Pat. No. 4,710,021. During the cell pulse and cell count acquisition phase of each sample analysis cycle, as cells are drawn through the impedance aperture, fluid is drawn through the metering tube. When the reagent meniscus passes an optical detector, the pulse acquisition phase is started for simultaneous counting of thrombocytes and erythrocytes. Actually, the pulses for the two differing "windows of visibility" of FIGS. 4A and 4B are processed in two different electronic circuits and all the data are stored as digital values in so-called list-mode. This acquisition is stopped when the meniscus passes a second optical detector. Exactly 100 μL or 200 μL of diluted blood passes through the impedance transducer during this interval depending on the manometer selected for the instrument. The count time can be used to detect debris in the orifice since such material will reduce the effective aperture diameter and thus increase the count time. This debris might also adversely affect sizing data.

[The present invention is applicable to all the thrombocyte and erythrocyte impedance data illustrated with FIGS. 1 to 5 not only to the optic data detailed in FIGS. 10 and 11.]

The CELL-DYN® 3000 derives the mean cell volume (MCV) from the erythrocyte size distribution. The result is reported directly in the previously discussed EEEV femtoliters. The hemacrit result is reported as the percent packed erythrocytes or as the proportion of packed erythrocytes per unit volume of whole blood: L/L.

The EEEV femtoliter scale is established for any erythrocyte diluent and impedance analyzer by ensuring that the electronically obtained hematocrit agrees with the reference microhematocrit or Packed Cell Volume (PCV) obtained by centrifugation. For typical anti-coagulated fresh human blood samples such average agreement is achieved by scaling the erythrocyte pulses (which have been calibrated so that the hematocrit (HCT) calculated from the erythrocyte count and from the electronic MCV agree with the PCV.

$$HCT = (RBC\ count \times MCV)/10 = PCV$$

The red cell distribution width (RDW) is determined from the red cell volume distribution. It is simply a carefully extracted C.V. of the histogram peak expressed as percent [C.V. = (SD/mean) × 100]. This parameter is an index of red cell isocytosis and kilocytosis. The RDW varies both with the degree of anisocytosis seen on the blood smear (variation in erythrocyte size) and with the degree of poikilocytosis (variation in erythrocyte shape). All the above parameters are clinically useful results.

These results are displayed on the monitor at the completion of each sample processing or measurement cycle. The user has liberal control over the order and manner in which the results appear in this display and in printed reports. Excerpts from the four-dimensional light scatter data from lyse-surviving leukocytes may be displayed as two-dimensional scattergrams (as illustrated with FIG. 6) and/or as selectable histograms (not shown here but similar to those shown in FIG. 4). The absolute leukocyte count may be displayed in units of thousands/μL of whole blood or in other units such as SI units. Erythrocyte data is displayed as a volume frequency distribution histogram with the abscissa demarcated in EEEV femtoliters (as illustrated in FIG. 4B). The absolute erythrocyte count is displayed in units of millions/μL of whole blood or in other units such as SI units. Thrombocyte data is displayed as a volume frequency distribution histogram with the abscissa demarcated in LEEV femtoliters (as shown in FIG. 4A). The absolute thrombocyte count is reported in units of thousands/μL of whole blood or in other units including SI units.

CONTROL AND DATA PROCESSING FEATURES

The CELL-DYN® 3000 operations are controlled by three microprocessors which monitor system status, store data, run QC programs, flag abnormal data and perform diagnostic checks. The computer of the data station is used to calculate the cell decay rates used to interrogate all the cell population survivorship characteristics. The leukocyte decay rate needed to correct leukocyte population counts for inadvertent leukolysis is only one such rate.

The CELL-DYN® 3000 automatically displays a vast set of user selectable numeric and graphic data after each measurement cycle. Specimen measurements are performed by selecting the run mode. The specimen may be identified as follows: patient, low control, normal control, high control, replicate, sample type of choice, etc. Operator identification, date, time, etc. may be entered via the keyboard. Displayed data may be printed (a single report to the page) on Z-fold paper (8.5"×11") via a graphics printer. Alternatively, a multicopy ticket report may also be printed with the same printer.

Depending on the size selected for the computer's hard disk, digital summary data for the current 2,000 to 10,000 cycles is automatically stored. This data may be reviewed or printed as required. Each data file includes the graphic data and may include the following information: a sequence number, specimen type, specimen identification number (if used), date, time, operator identification and the numeric graphic data for all of the parameters which were selected by the operator from those described above. Additional numeric data may include instrument monitoring parameters and the cell population decay rate monitoring parameters of the present invention.

The setup mode allows the user to set limits for any numeric data. Any data falling outside these limits are displayed in user selectable highlighted color on the video screen and are printed in bold type on reports. When the kinetically monitored data for erythrocytes and thrombocytes or the for four-dimensional scattergram data for lyse-surviving nucleated leukocytes do not meet certain criteria, each affected region is flagged with a fully interpreted alert message.

While certain representative embodiments and details have been shown for the purpose of illustrating the invention, various changes and modifications may be made therein without departing from the scope of the invention as defined in the appended claims.

We claim:

1. A method for accurately estimating the number of cells initially present per unit volume in a first cell population in a sample solution having at least two cell populations said method comprising the steps of:
    a) providing a sample solution having a first cell population and a second cell population;
    b) adjusting the physico-chemical conditions of said sample solution at time zero to completely and substantially instantaneously lyse all of the cells in said second cell population and to kinetically lyse the cells in the first cell population;
    c) counting the number of cells in said first cell population per unit volume of the sample solution at a time interval A after time zero;
    d) counting the number of cells in said first cell population per unit volume of the sample solution at a time interval B after time zero and after time interval A;

e) calculating a first cell population cell decay rate as a function of time using the cell counts from steps (c) and (d) and time intervals A and B; and, f) estimating the number of cells initially present in said first cell population per unit volume of sample solution by back extrapolating the calculated first cell population cell decay rate function to time zero.

2. A method as recited in claim 1 wherein said sample solution is a member of the group consisting of physiologic fluids, organ cell suspensions, plant cell suspensions, animal cell suspensions, cell culture in media and mixtures thereof.

3. A method as recited in claim 1 wherein said first cell population is leukocytes and said second cell population is erythrocytes.

4. A method as recited in claim 1 wherein said adjustment step (b) includes contacting said sample solution with a lysing agent.

5. A method as recited in claim 1 wherein said cell counting step is accomplished by measuring an electrical impedance across an orifice through which the sample solution is caused to flow, and processing the number and intensity of the pulses to provide enumeration data.

6. A method as recited in claim 1 wherein said cell counting step is accomplished by passing the sample solution through a flow cell where it is intersected with a laser beam and by collecting and processing light scattering data from said flow cell to provide enumeration data.

7. A method as recited in claim 1 wherein said cell decay rate calculation utilizes linear curve fitting techniques.

8. A method for accurately estimating the number of cells initially present per unit volume in a first cell population in the presence of a second cell population in a sample solution having at least two cell populations, wherein said first cell population exhibits a continuous kinetic rate of cytolysis as a function of time and wherein said second cell population undergoes substantially instantaneous and total cytolysis when said sample solution physico-chemical conditions are adjusted to exceed a cytolytic threshold of said second cell population, said method comprising the steps of:

a) providing a sample solution having a first cell population and a second cell population;

b) providing means for identifying, categorizing and enumerating the cells in said first cell population per unit volume of sample solution;

c) adjusting the physico-chemical conditions of said sample solution such that the cytolytic threshold of said second cell population is exceeded to thereby completely and substantially instantaneously lyse all of the cells in said second cell population at time zero;

d) identifying, categorizing and enumerating the first cell population cells per unit volume present in a first discrete volume of said adjusted sample solution at time interval A after time zero using said means provided in step (b);

e) identifying, categorizing and enumerating the first cell population cells per unit volume present in a second discrete volume of said adjusted sample solution at time interval B after time zero and after time interval A using said means provided in step (b);

f) calculating a first cell population cell decay rate as a function of time using the cell enumeration data obtained in steps (d) and e) and the time intervals A and B; and, g) estimating the number of cells initially present in said first cell population per unit volume of sample solution by back extrapolating said calculated first cell population cell decay rate function to time zero.

9. A method as recited in claim 8 wherein said sample solution is a member of the group consisting of physiologic fluids, organ cell suspensions, plant cell suspensions, animal cell suspensions, cell culture in media and mixtures thereof.

10. A method as recited in claim 8 wherein said first cell population is leukocytes and said second cell population is erythrocytes.

11. A method as recited in claim 8 wherein said adjustment step (c) includes contacting said sample solution with a lysing agent.

12. A method as recited in claim 8 wherein said cell identifying, categorizing and enumerating step is accomplished by measuring an electrical impedance across an orifice through which the sample solution is caused to flow, and processing the number and intensity of the pulses to provide enumeration data.

13. A method as recited in claim 8 wherein said cell identifying, categorizing and enumerating step is accomplished by passing the sample solution through a flow cell where it is intersected with a laser beam and by collecting and processing light scattering data from said flow cell to provide enumeration data.

14. A method as recited in claim 8 wherein said cell decay rate calculation utilizes linear curve fitting techniques.

15. A method for accurately estimating the number of cells initially present per unit volume of sample solution in a first cell population and in a second cell population in the sample solution in which said first cell populations and second cell population continuously kinetically decay in a diluted sample solution at different decay rates resulting from the physics-chemical conditions caused by dilution of the sample solution, said method comprising the steps of:

a) providing a sample solution having a first cell population and a second cell population;

b) diluting said sample solution at time zero, said dilution step causing cells in both said first and second cell populations to commence continuous kinetic lysing because of changed physics-chemical conditions in the sample solution, c) counting the number of cells in each of said first and second cell populations per unit volume of sample solution present in a first discrete volume of diluted sample at time interval A after time zero;

d) counting the number of cells in each of said first and second cell populations per unit volume of sample solution present in a second discrete volume of diluted sample solution at time interval B after time zero, and after time interval A;

e) calculating for each of said first and second cell populations a cell decay rake as a function of time using said cell counts from steps c) and d) and time intervals A and B; and f) estimating the number of cells initially present in each of said first and second cell populations per unit volume of sample solution by back extrapolating the respective cell decay rate functions to time zero.

16. A method as recited in claim 15 wherein said sample solution is a member of the group consisting of physiologic fluids, organ cell suspensions, plant cell suspensions, animal cell suspensions, cell culture in media and mixtures thereof.

17. A method as recited in claim 15 wherein said first cell population is leukocytes and said second cell population is erythrocytes.

18. A method as recited in claim 15 wherein said dilution step (b) includes contacting said sample solution with a lysing agent.

19. A method as recited in claim 15 wherein said cell counting step is accomplished by measuring an electrical impedance across an orifice through which the sample solution is caused to flow, and processing the number and intensity of the pulses to provide enumeration data.

20. A method as recited in claim 15 wherein said cell counting step is accomplished by passing the sample solution through a flow cell where it is intersected with a laser beam and by collecting and processing light scattering data from said flow cell to provide enumeration data.

21. A method as recited in claim 15 wherein said cell decay rate calculation utilizes linear curve fitting techniques.

22. A method as recited in claim 15 wherein said sample solution is obtained from a human fetal patient or a neonatal patient, and said sample solution exhibits erythrolytic-resistant behavior.

23. A method for accurately estimating the number of cells initially present per unit volume of a sample solution in a first cell population and in a second cell population in which said first cell population and said second cell population exhibit different continuous kinetic rates of cytolysis as a function of time and wherein cells in said first cell population and in said second cell population undergo cytolysis when said sample solution physico-chemical conditions are adjusted to exceed a cytolytic threshold for cells in said second cell population, said method comprising the steps of:
   a) providing a sample solution having a first cell population and a second cell population;
   b) providing means for identifying, categorizing and enumerating the cells in said first cell population and in said second cell population per unit volume of sample solution;
   c) adjusting the physico-chemical conditions of said sample solution such that the cytolytic threshold for cells in said second cell population is exceeded to thereby commence lysing of the cells in said second cell population at time zero;
   d) identifying, categorizing and enumerating the first cell population cells per unit volume of sample solution and the second cell population cells per unit volume of sample solution present in a first discrete volume of said adjusted sample solution at time interval A after time zero using said means provided in step (b);
   e) identifying, categorizing and enumerating the first cell population cells per unit volume of sample solution and the second cell population cells per unit volume of sample solution present in a second discrete volume of said adjusted sample solution at time interval B after time zero, and after time interval A using said means provided in step (b);
   f) calculating for each of said cell populations a cell population cell decay rate as a function of time using the cell enumeration data obtained in steps (d) and (e) and the time intervals A and B; and,
   g) estimating the number of cells initially present in each of said cell populations per unit volume of sample solution by back extrapolating the respective cell decay rate functions to time zero.

24. A method as recited in claim 23 wherein said sample solution is a member of the group consisting of physiologic fluids, organ cell suspensions, plant cell suspensions, animal cell suspensions, cell culture in media and mixtures thereof.

25. A method as recited in claim 23 wherein said first cell population is leukocytes and said second cell population is erythrocytes.

26. A method as recited in claim 23 wherein said adjustment step (c) includes contacting said sample solution with a lysing agent.

27. A method as recited in claim 23 wherein said cell identifying, categorizing and enumerating step is accomplished by measuring an electrical impedance across an orifice through which the sample solution is caused to flow, and processing the number and intensity of the pulses to provide enumeration data.

28. A method as recited in claim 23 wherein said cell identifying, categorizing and enumerating step is accomplished by passing the sample solution through a flow cell where it is intersected with a laser beam and by collecting and processing light scattering data from said flow cell to provide enumeration data.

29. A method as recited in claim 23 wherein said cell decay rate calculation utilizes linear curve fitting techniques.

30. A method for identifying, categorizing and enumerating cells in a sample solution also containing lyse-resistant erythrocytes which comprises the steps of:
   a) providing a sample solution containing cells, erythrocytes and lyse-resistant erythrocytes;
   b) contacting said sample solution with an erythrolytic agent at time zero to completely and substantially instantaneously lyse all erythrocytes including said lyse-resistant erythrocytes and to kinetically lyse the cells remaining being enumerated;
   c) providing means for identifying, categorizing and enumerating the lyse-surviving cells present per unit volume of said sample solution;
   d) identifying, categorizing and enumerating lyse-surviving cells per unit volume of sample solution present in a first discrete volume of said sample solution at time interval A after time zero using said means provided in step (c);
   e) identifying, categorizing and enumerating lyse-surviving cells per unit volume of sample solution present in a second discrete volume of said sample solution at time interval B after time zero, and after time interval A using said means provided in step (c);
   f) calculating a lyse-surviving cell decay rate as a function of time using the cell enumeration data obtained in steps (d) and (e) and the time intervals from erythrolytic agent addition in step (b) to said respective counts; and,
   g) estimating the number of lyse-surviving cells initially present per unit volume of sample solution by back extrapolating said calculated cell decay rate function to time zero.

31. A method as recited in claim 30 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

32. A method as recited in claim 30 wherein said erythrolytic agent consists essentially of an aqueous solution of 2-phenoxyethanol, TRIS/HCl buffer and Triton X-100 detergent compound.

33. A method as recited in claim 30 wherein said sample solution is a member of the group consisting of physiologic fluids, organ cell suspensions, animal cell suspensions, cell culture in media and mixtures thereof.

34. A method as recited in claim 30 wherein said cell identifying, categorizing and enumerating step is accomplished by measuring an electrical impedance across an orifice through which the sample solution is caused to flow, and processing the number and intensity of the pulses to provide enumeration data.

35. A method as recited in claim 30 wherein said cell identifying, categorizing and enumerating step is accomplished by passing the sample solution through a flow cell where it is intersected with a laser beam and by collecting and processing light scattering data from said flow cell to provide enumeration data.

36. A method as recited in claim 30 wherein said cell decay rate calculation utilizes linear curve fitting techniques.

37. A method for identifying, categorizing and enumerating leukocytes present in a whole blood sample also containing lyse-resistant erythrocytes which comprises the steps of:
a) providing a whole blood sample containing erythrocytes, lyse-resistant erythrocytes and leukocytes;
b) forming a sample solution by contacting said whole blood sample with an erythrolytic agent at time zero to completely and substantially instantaneously lyse all erythrocytes including said lyse-resistant erythrocytes and to kinetically lyse the leukocytes present in the sample solution;
c) providing leukocyte identifying, categorizing and enumerating means;
d) identifying, categorizing and enumerating the lyse-surviving leukocytes per unit volume of sample present in a first portion of said sample solution at time interval A after time zero using said identifying, categorizing and enumerating means provided in step (c);
e) identifying, categorizing and enumerating the lyse-surviving leukocytes per unit volume of sample present in a second portion of said sample solution at time interval B after time zero, and after time interval A using said identifying categorizing and enumerating means provided in step (c);
f) calculating a leukocyte decay rate as a function of time using the cell enumeration data obtained in steps (d) and (e) and the time intervals A and B; and,
g) estimating the number of leukocytes initially present per unit volume of sample by back extrapolating said leukocyte decay rate function to time zero.

38. A method as recited in claim 37 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

39. A method as recited in claim 37 wherein said erythrolytic agent consists essentially of an aqueous solution of 2-phenoxyethanol, TRIS/HCl buffer and Triton X-100 detergent compound.

40. A method as recited in claim 37 wherein said cell identifying, categorizing and enumerating step is accomplished by measuring an electrical impedance across an orifice through which the sample solution is caused to flow, and processing the number and intensity of the pulses to provide enumeration data.

41. A method as recited in claim 37 wherein said cell identifying, categorizing and enumerating step is accomplished by passing the sample solution through a flow cell where it is intersected with a laser beam and by collecting and processing light scattering data from said flow cell to provide enumeration data.

42. A method as recited in claim 37 wherein said cell decay rate calculation utilizes linear curve fitting techniques.

43. A method for identifying, categorizing and enumerating leukocyte subpopulations present in a whole blood sample also containing lyse-resistant erythrocytes which comprises the steps of:
a) providing means for identifying, categorizing and enumerating leukocyte subpopulations;
b) providing a whole blood sample containing erythrocytes, lyse-resistant erythrocytes and leukocytes;
c) forming a sample solution by contacting said whole blood sample with an erythrolytic agent at time zero to completely and substantially instantaneously lyse all erythrocytes including said lyse-resistant erythrocytes and to kinetically lyse the leukocytes present in the sample solution;
d) passing a first discrete volume of said sample solution through said identifying, categorizing and enumerating means to obtain an enumeration of the lyse-surviving cells present in each leukocyte subpopulation per unit volume of sample at time interval A after time zero;
e) passing a second discrete volume of said sample solution through said identifying, categorizing and enumerating means to obtain an enumeration of the lyse-surviving cells present in each leukocyte subpopulation per unit volume of sample at time interval B after time zero, and after time interval A;
f) for each leukocyte subpopulation identified, categorized and enumerated in steps (d) and (e), calculating a cell decay rate as a function of time using said cell subpopulation enumeration data and the time intervals A and B; and,
g) for each leukocyte subpopulation identified, categorized and enumerated in steps (d) and (e), estimating the number of cells initially present in each subpopulation per unit volume of sample by back extrapolating said respective calculated specific cell population cell decay rate function to time zero.

44. A method as recited in claim 43 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

45. A method as recited in claim 43 wherein said erythrolytic agent consists essentially of an aqueous solution of 2-phenoxyethanol, TRIS/HCl buffer and Triton X-100 detergent compound.

46. A method as recited in claim 43 wherein said passing and leukocyte subpopulation enumerating steps are accomplished by measuring an electrical impedance across an orifice through which the sample solution is caused to flow, and processing the number and intensity of the pulses to provide enumeration data.

47. A method as recited in claim 43 wherein said passing and leukocyte subpopulation enumerating steps are accomplished by passing the sample solution through a flow cell where it is intersected with a laser beam and by collecting and processing light scattering data from said flow cell to provide enumeration data.

48. A method as recited in claim 43 wherein said cell decay rate calculation utilizes linear curve fitting techniques.

49. A method for identifying, categorizing and enumerating leukocytes present in a whole blood sample which contains fragile leukocytes which comprises the steps of:
   a) providing a whole blood sample containing erythrocytes leukocytes and fragile leukocytes;
   b) forming a sample solution by contacting said whole blood sample with an erythrolytic agent at time zero to completely and substantially instantaneously lyse said erythrocytes and to kinetically lyse the leukocytes present in the sample solution;
   c) providing leukocyte identifying, categorizing and enumerating means;
   d) identifying, categorizing and enumerating the lyse-surviving leukocytes per unit volume of sample present in a first portion of said sample solution at time interval A after time zero using said identifying, categorizing and enumerating means provided in step (c);
   e) identifying, categorizing and enumerating the lyse-surviving leukocytes per unit volume of sample present in a second portion of said sample solution at time interval B after time zero which occurs subsequent to time interval A using said identifying, categorizing and enumerating means provided in step (c);
   f) calculating a leukocyte decay rate as a function of time using the leukocyte enumeration data obtained in steps (d) and (e) and the time intervals A and B; and,
   g) estimating the number of leukocytes initially present per unit volume of sample by back extrapolating said leukocyte decay rate function to time zero.

50. A method as recited in claim 49 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

51. A method as recited in claim 49 wherein said erythrolytic agent consists essentially of an aqueous solution of 2-phenoxyethanol, TRIS/HCl buffer and Triton X-100 detergent compound.

52. A method as recited in claim 49 wherein said cell identifying, categorizing and enumerating step is accomplished by measuring an electrical impedance across an orifice through which the sample solution is caused to flow, and processing the number and intensity of the pulses to provide enumeration data.

53. A method as recited in claim 49 wherein said cell identifying, categorizing and enumerating step is accomplished by passing the sample solution through a flow cell where it is intersected with a laser beam and by collecting and processing light scattering data from said flow cell to provide enumeration data.

54. A method as recited in claim 49 wherein said cell decay rate calculation utilizes linear curve fitting techniques.

55. A method for identifying, categorizing and enumerating leukocyte subpopulations present in a whole blood sample containing erythrocytes and fragile leukocytes which comprises the steps of:
   a) providing means for identifying, categorizing and enumerating leukocyte subpopulations;
   b) providing a whole blood sample containing erythrocytes leukocytes and fragile leukocytes;
   c) forming a sample solution by contacting said whole blood sample with an erythrolytic agent at time zero to completely and substantially instantaneously lyse said erythrocytes and to kinetically lyse the leukocytes present in the sample solution;
   d) passing a first discrete volume of said sample solution through said identifying, categorizing and enumerating means to obtain an enumeration of lyse-surviving cells per unit volume of sample present in each leukocyte subpopulation at time interval A after time zero;
   e) passing a second discrete volume of said sample solution through said identifying, categorizing and enumerating means to obtain an enumeration of lyse-surviving cells per unit volume of sample present in each leukocyte subpopulation at time interval B after time zero, and after time interval A;
   f) for each leukocyte subpopulation identified, categorized and enumerated in steps (d) and (e), calculating a cell decay rate as a function of time using said cell enumeration data and time intervals A and B; and,
   g) for each leukocyte subpopulation identified, categorized and enumerated in steps (d) and (e), estimating the number of leukocytes initially present per unit volume of sample by back extrapolating said respective calculated cell decay rate function to time zero.

56. A method as recited in claim 55 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

57. A method as recited in claim 55 wherein said erythrolytic agent consists essentially of an aqueous solution of 2-phenoxyethanol, TRIS/HCl buffer and Triton X-100 detergent compound.

58. A method as recited in claim 55 wherein said passing and leukocyte subpopulation enumerating steps are accomplished by measuring an electrical impedance across an orifice through which the sample solution is caused to flow, and processing the number and intensity of the pulses to provide enumeration data.

59. A method as recited in claim 55 wherein said passing and leukocyte subpopulation enumerating steps are accomplished by passing the sample solution through a flow cell where it is intersected with a laser beam and by collecting and processing light scattering data from said flow cell to provide enumeration data.

60. A method as recited in claim 55 wherein said cell decay rate calculation utilizes linear curve fitting techniques.

61. A method for identifying, categorizing and enumerating leukocyte subpopulations present in a whole blood sample also containing erythrocytes and fragile leukocytes which comprises the steps of:
   a) providing a whole blood sample containing erythrocytes and leukocytes;
   b) providing a flow system having a detector region through which a sample solution can flow substantially cell by cell, a detector which detects a signal generated by the cells flowing through the detector region and a processor which processes said detected signal to identify, to categorize and to enumerate leukocyte subpopulations in said whole blood sample;
   c) forming a sample solution by contacting said whole blood sample with an erythrolytic agent at time zero to completely and substantially instantaneously lyse said erythrocytes and to kinetically lyse the leukocytes present in the sample solution;
   d) passing a first discrete volume of said sample solution through said flow system to obtain an enumeration of the cells in each lyse-surviving leukocyte subpopulation per unit volume of sample present at time interval A after time zero;
   e) passing a second discrete volume of said sample solution through said flow system to obtain an enumeration of the lyse-surviving cells per unit volume of sample present in each leukocyte subpopulation at time interval B after time zero, and after time interval A;
   f) for each leukocyte subpopulation identified, categorized and enumerated in steps (d) and (e), calculating a cell decay rate as a function of time using said cell enumeration data and the time intervals A and B; and,
   g) for each leukocyte subpopulation identified, categorized and enumerated in steps (d) and (e), estimating the number of leukocytes initially present per unit volume of sample by back extrapolating said respective cell decay rate function to time zero.

62. A method as recited in claim 61 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

63. A method as recited in claim 61 wherein said erythrolytic agent consists essentially of an aqueous solution of 2-phenoxyethanol, TRIS/HCl buffer and Triton X-100 detergent compound.

64. A method as recited in claim 61 wherein said passing and leukocyte subpopulation enumerating steps are accomplished by measuring an electrical impedance across an orifice through which the sample solution is caused to flow, and processing the number and intensity of the pulses to provide enumeration data.

65. A method as recited in claim 61 wherein said passing and leukocyte subpopulation enumerating steps are accomplished by passing the sample solution through a flow cell where it is intersected with a laser beam and by collecting and processing light scattering data from said flow cell to provide enumeration data.

66. A method as recited in claim 61 wherein said cell decay rate calculation utilizes linear curve fitting techniques.

67. A method for identifying, categorizing and enumerating leukocyte subpopulations present in a whole blood sample also containing erythrocytes and fragile leukocytes which comprises the steps of:
   a) providing a whole blood sample containing erythrocytes and leukocytes;
   b) providing a flow system having a detector region through which a sample solution can flow substantially cell by cell, an impedance detector which detects a signal generated by the cells flowing through the detector region, and a processor which processes said detected signal to identify, to categorize and to enumerate leukocyte subpopulations in said whole blood sample;
   c) forming a sample solution by contacting said whole blood sample with an erythrolytic agent at time zero to completely and substantially instantaneously lyse said erythrocytes and to kinetically lyse the leukocytes present in the sample solution;
   d) passing a first discrete volume of said sample solution through said flow system to obtain an enumeration of the cells in each lyse-surviving leukocyte subpopulation per unit volume of sample present at time interval A after time zero;
   e) passing a second discrete volume of said sample solution through said flow system to obtain an enumeration of the lyse-surviving cells per unit volume of sample present in each leukocyte subpopulation at time interval B after time zero, and after time interval A;
   f) for each leukocyte subpopulation identified, categorized and enumerated in steps (d) and (e), calculating a specific cell population cell decay rate as a function of time using said cell enumeration data and the time intervals A and B; and,
   g) for each leukocyte subpopulation identified, categorized and enumerated in steps (d) and (e), estimating the number of cells initially present in each subpopulation per unit volume of sample by back extrapolating said respective calculated specific cell population cell decay rate function to time zero.

68. A method as recited in claim 67 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

69. A method as recited in claim 67 wherein said erythrolytic agent consists essentially of an aqueous solution of 2-phenoxyethanol, TRIS/HCl buffer and Triton X-100 detergent compound.

70. A method as recited in claim 67 wherein said passing and leukocyte subpopulation enumerating steps are accomplished by measuring an electrical impedance across an orifice through which the sample solution is caused to flow, and processing the number and intensity of the pulses to provide enumeration data.

71. A method as recited in claim 67 wherein said passing and leukocyte subpopulation enumerating steps are accomplished by passing the sample solution through a flow cell where it is intersected with a laser beam and by collecting and processing light scattering data from said flow cell to provide enumeration data.

72. A method as recited in claim 67 wherein said cell decay rate calculation utilizes linear curve fitting techniques.

73. A method for identifying, categorizing and enumerating leukocyte subpopulations present in a whole blood sample also containing erythrocytes and fragile leukocytes which comprises the steps of:
   a) providing a whole blood sample containing erythrocytes and leukocytes;
   b) providing a flow system having a flow cell through which a sample solution can flow substantially cell by cell, a light source, a photometric unit for detecting light signals issuing from cells and an analyzer for analyzing and processing the light signals to obtain an identification, categorization and enumeration of leukocyte subpopulations in said sample;
   c) forming a sample solution by contacting said whole blood sample with an erythrolytic agent at time zero to completely and substantially instantaneously lyse said erythrocytes and to kinetically lyse the leukocytes present in the sample solution;
   d) passing a first discrete volume of said sample solution through said flow system to obtain an enumeration of the cells in each lyse-surviving leukocyte subpopulation per unit volume of sample present at time interval A after time zero;
   e) passing a second discrete volume of said sample solution through said flow system to obtain an enumeration of lyse-surviving cells per unit volume of sample present in each leukocyte subpopulation at time interval B after time zero, and after time interval A;
   f) for each leukocyte subpopulation identified, categorized and enumerated in steps (d) and (e), calculating a specific cell population cell decay rate as a function of time using said cell enumeration data and the time intervals A and B; and,
   g) for each leukocyte subpopulation identified, categorized and enumerated in steps (d) and (e), estimating the number of cells initially present in each subpopulation per unit volume of sample by back extrapolating said respective calculated specific cell population cell decay rate function to time zero.

74. A method as recited in claim 73 wherein said erythrolytic agent consists essentially of an aqueous solution of (i) an aromatic oxyethanol; (ii) an organic buffer with pK at or near 8.5, serving to provide pH buffering capacity and to increase the electrical conductivity of the lytic agent; and, (iii) a non-ionic detergent compound.

75. A method as recited in claim 73 wherein said erythrolytic agent consists essentially of an aqueous solution of 2-phenoxyethanol, TRIS/HCl buffer and Triton X-100 detergent compound.

76. A method as recited in claim 73 wherein said passing and leukocyte subpopulation enumerating steps are accomplished by measuring an electrical impedance across an orifice through which the sample solution is caused to flow, and processing the number and intensity of the pulses to provide enumeration data.

77. A method as recited in claim 73 wherein said passing and leukocyte subpopulation enumerating steps are accomplished by passing the sample solution through a flow cell where it is intersected with a laser beam and by collecting and processing light scattering data from said flow cell to provide enumeration data.

78. A method as recited in claim 73 wherein said cell decay rate calculation utilizes linear curve fitting techniques.

79. A method for characterizing the lytic behavior of an erythrocyte population present in a blood sample which comprises the steps of:
   a) providing a sample solution having an erythrocyte population;
   b) providing means for identifying and enumerating the erythrocytes per unit volume of sample solution;
   c) adjusting the physico-chemical conditions of said sample solution such that a cytolytic threshold for said erythrocytes is exceeded to thereby commence erythrolysis at time zero;
   d) identifying and enumerating the erythrocytes per unit volume present in a first discrete volume of said adjusted sample solution at time interval A after time zero using said means provided in step (b);
   e) identifying and enumerating the erythrocytes per unit volume present in a second discrete volume of said adjusted sample solution at time interval B after time zero, and after time interval A using said means provided in step (b); and,
   f) calculating an erythrocyte decay rate as a function of time using the erythrocyte enumeration data obtained in steps (d) and (e) and the time intervals A and B.

* * * * *